(12) United States Patent
Ordentlich et al.

(10) Patent No.: US 12,000,829 B2
(45) Date of Patent: Jun. 4, 2024

(54) SELECTION OF PATIENTS FOR COMBINATION THERAPY

(71) Applicant: SYNDAX PHARMACEUTICALS, INC., Waltham, MA (US)

(72) Inventors: Peter Ordentlich, Lexington, MA (US); Lei Wang, Waltham, MA (US); Serap Sankoh, Waltham, MA (US); Michael Meyers, Waltham, MA (US)

(73) Assignee: Syndax Pharmaceuticals, Inc., Waltham, MA (US)

( * ) Notice: Subject to any disclaimer, the term of this patent is extended or adjusted under 35 U.S.C. 154(b) by 853 days.

(21) Appl. No.: 17/053,559

(22) PCT Filed: May 7, 2019

(86) PCT No.: PCT/US2019/031210
§ 371 (c)(1),
(2) Date: Nov. 6, 2020

(87) PCT Pub. No.: WO2019/217484
PCT Pub. Date: Nov. 14, 2019

(65) Prior Publication Data
US 2021/0239697 A1    Aug. 5, 2021

Related U.S. Application Data

(60) Provisional application No. 62/668,055, filed on May 7, 2018.

(51) Int. Cl.
| | |
|---|---|
| *G01N 33/569* | (2006.01) |
| *A61K 9/00* | (2006.01) |
| *A61K 31/4406* | (2006.01) |
| *A61K 39/395* | (2006.01) |
| *A61P 35/00* | (2006.01) |
| *G01N 33/574* | (2006.01) |
| *A61K 39/00* | (2006.01) |

(52) U.S. Cl.
CPC ..... *G01N 33/56977* (2013.01); *A61K 9/0019* (2013.01); *A61K 9/0053* (2013.01); *A61K 31/4406* (2013.01); *A61K 39/3955* (2013.01); *A61P 35/00* (2018.01); *G01N 33/56972* (2013.01); *G01N 33/57423* (2013.01); *A61K 2039/54* (2013.01); *A61K 2039/545* (2013.01); *G01N 2333/70535* (2013.01); *G01N 2333/70539* (2013.01); *G01N 2333/70596* (2013.01); *G01N 2800/52* (2013.01)

(58) Field of Classification Search
CPC ....... G01N 33/56977; G01N 33/56972; G01N 33/57423; G01N 2333/70535; G01N 2333/70539; G01N 2333/70596; G01N 2800/52; G01N 33/5743; A61K 9/0019; A61K 9/0053; A61K 31/4406; A61K 39/3955; A61K 2039/54; A61K 2039/545; A61P 35/00

See application file for complete search history.

(56) References Cited

U.S. PATENT DOCUMENTS

| | | |
|---|---|---|
| 8,500,712 B2 | 8/2013 | Polettini et al. |
| 10,226,472 B2 | 3/2019 | Goodenow et al. |
| 11,397,184 B2 | 7/2022 | Ordentlich |
| 2012/0070461 A1 | 3/2012 | Singh et al. |
| 2012/0276004 A1 | 11/2012 | Epstein et al. |
| 2014/0378420 A1 | 12/2014 | Goodenow et al. |
| 2023/0061048 A1 | 3/2023 | Ordentlich |

FOREIGN PATENT DOCUMENTS

| | | | |
|---|---|---|---|
| JP | 2014507005 A | 3/2014 | |
| WO | WO-2013033656 A1 | 3/2013 | |
| WO | WO-2014011713 A2 | 1/2014 | |
| WO | WO-2014085461 A1 | 6/2014 | |
| WO | WO-2016010879 A1 | 1/2016 | |
| WO | WO-2016154068 A1 | 9/2016 | |
| WO | WO 2017/041043 * | 3/2017 | ........... G01N 33/574 |
| WO | WO-2017041043 A1 | 3/2017 | |

OTHER PUBLICATIONS

Johnson et al. (ASCO Annual Meeting I, Abstract e20659, May 20, 2016) (Year: 2016).*
Ang Huang et al. "Increased CD14(+)HLA-DR(-/low) myeloid-derived suppressor cells correlate with extrathoracic metastasis and poor response to chemotherapy in non-small cell lung cancer patients," Cancer Immunol Immunother. vol. 62, No. 9, 2013, pp. 1439-1451.
Bergenfelz, C., et al., "Systemic Monocytic-MDSCs Are Generated from Monocytes and Correlate with Disease Progression in Breast Cancer Patients, " PLoS One, 2015, vol. 10(5), pp. 1-23.
Invitation to Pay Additional Fees for International Application No. PCT/US2019/031210, dated Jul. 22, 2019, 12 pages.
Kim et al. "Eradication of metastatic mouse cancers resistant to immune checkpoint blockade by suppression of myeloid-derived cells". Proceedings of the National Academy of Sciences, (2014); 111(32):11774-11779.
Krieg, C., "High-dimensional single-cell analysis predicts response to anti-PD-1 immunotherapy", Nature Medicine, 2018, vol. 24, No. 2, pp. 144-154.
Lin, Y. et al. "Immunosuppressive CD14+HLA-DRlow/-monocytes in B-cell non-Hodgkin lymphoma," Blood, (2011); 117(3):872-881.
Orillion et al. "Entinostat Neutralizes Myeloid-Derived Suppressor Cells and Enhances the Antitumor Effect of PD-1 Inhibition in Murine Models of Lung and Renal Cell Carcinoma," Clinical Cancer Research, (2017); 23(17):5187-5201.

(Continued)

*Primary Examiner* — Nelson B Moseley, II
(74) *Attorney, Agent, or Firm* — COOLEY LLP; Heidi A. Erlacher; Eric A. Owens

(57) ABSTRACT

Described herein are methods for selecting cancer patients for treatment with a combination therapy comprising an HDAC inhibitor and a second therapeutic agent. In particular, methods are provided for the examination of a non-cancer cell type which are CD14-positive, HLA-DR-high and/or CD16-negative, as a therapeutic indicator in the setting of HDAC inhibitor combination therapies.

18 Claims, 8 Drawing Sheets

(56) References Cited

OTHER PUBLICATIONS

Rudolph et al, "Increased frequencies of CD11b+ CD33+CD14+ HLA-DRlow myeloid-derived suppressor cells are an early event in melanoma patients", Experimental Dermatology, (2014), 23:199-218.

Shen et al. "Class I histone deacetylase inhibitor entinostat suppresses regulatory T cells and enhances immunotherapies in renal and prostate cancer models," PloS One, (2012); 7(1):e30815, 14 pages.

Suraweera et al. "Combination Therapy With Histone Deacetylase Inhibitors (HDACi) for the Treatment of Cancer: Achieving the Full Therapeutic Potential of HDACi," Frontiers in Oncology, (2018); 8(92):1-15.

Syndax Pharmaceuticals et al. "Syndax Announces Updated Results from Phase 2 Encore 601 Trial of Entinostat in Combination with Keytruda (pembrolizumab)," (2018); 5 pages. Retrieved from the Internet: URL:https://www.prnewswire.com/news-releases/syndax-announcesupdated-results-from-phase-2-encore-601-trial-of-entinostat-incombination-with-keytruda-pembrolizumab-300650233.html.

Thurn, K.T. et al., "Rational Therapeutic Combinations with Histone Deacetylase Inhibitors for the Treatment of Cancer," Future Oncology, (2011); 7(2):1-34.

Tomita et al. "The interplay of epigenetic therapy and immunity in locally recurrent or metastatic estrogen receptor-positive breast cancer: Correlative analysis of Encore 301, a randomized, placebo-controlled phase II trial of exemestane with or without entinostat," Oncoimmunology, (2016); 5(11):e1219008, 12 pages.

Tsang et al. "Antibody dependent cellular cytotoxicity activity of a novel anti-PD-L1 antibody, avelumab (MSB0010718C), on human tumor cells," 2015 ASCO Annual Meeting I, J. Clin. Oncol. (2015); 33:suppl; Abstract 3038, 3 pages. https://ascopubs.org/doi/10.1200/jco.2015.33.15_suppl.3038.

Vetsika, E. et al. "A Circulating Subpopulation of Monocytic Myeloid-Derived Suppressor Cells as an Independent Prognostic/Predictive Factor in Untreated Non-Small Lung Cancer Patients," Journal of Immunology Research, (2014); 2014(659294):12 pages.

Wang et al. "FOXP3+ regulatory T cell development and function require histone/protein deacetylase 3," The Journal of Clinical Investigation, (2015); 125(3):1111-1123.

Yardley, D.A., et al., "PD01-04: Entinostat, a Novel Histone Deacetylase Inhibitor, Added to Exemestane Improves PFS in Advanced Breast Cancer in a Randomized, Phase II, Double-Blind Study," Cancer Res, (2011); 71(24_Supplement):1-5.

"Syndax and Merck to collaborate on immuno-oncology study evaluating entinostat in combination with Keytruda in lung cancer and melanoma," 2015, 5 pages. Retrieved online: https://www.europeanpharmaceuticalreview.com/news/30492/syndax-and-merck-to-collaborate-on-immunooncology-study-evaluating-entinostat-in-combinationwith-keytmda-in-lung-cancer-and-melanoma.

Youn et al. "Epigenetic silencing of retinoblastoma gene regulates pathologic differentiation of myeloid cells in cancer," Nature Immunology, (2013); 14(3):211-220.

Clinical Trial NCT02437136, "Ph1b/2 Dose-Escalation Study of Entinostat With Pembrolizumab in NSCLC With Expansion Cohorts in NSCLC and Melanoma", SNDX-275-0601, (May 4, 2015), 16 pages.

Johnson et al., "Encore 601: A Phase 2 study of entinostat (ENT) in combination with pembrolizumab (PEMBRO) in patients with melanoma," Poster presented at the American Society of Clinical Oncology Annual Meeting, Jun. 2-6, 2017, [retrieved online Oct. 16, 2023], URL: https://www.syndax.com/wp-content/uploads/2017/06/Johnson-601-ASCO-2017-poster-final.pdf, 1 page.

Krieg C. et al., High dimensional single-cell analysis identifies classical monocyte frequencies to be predictive of progression free survival to anti-PD-1 immunotherapy. Pigment cell & melanoma Research, Published: Dec. 22, 2017, pp. 177-178. Wiley, SMR Congress 2017 abstracts, 106 pages, https://doi.org/10.1111/pcmr.12656.

* cited by examiner

SELECTION OF PATIENTS FOR COMBINATION THERAPY

RELATED APPLICATIONS

This application is a U.S. National Stage Application under 35 U.S.C. § 371 of International Application No. PCT/US19/31210, filed on May 7, 2019, which claims the benefit of and priority to U.S. Provisional Application No. 62/668,055, filed May 7, 2018, the contents of which are hereby incorporated by reference in their entireties.

INCORPORATION BY REFERENCE

All publications, patents, and patent applications described in this specification are herein incorporated by reference to the same extent as if each individual publication, patent, or patent application was specifically and individually indicated to be incorporated by reference.

BACKGROUND

Cancer, tumors, tumor-related disorders, and neoplastic disease states are serious and often times life-threatening conditions. These diseases and disorders, which are characterized by rapidly-proliferating cell growth, continue to be the subject of research efforts directed toward the identification of therapeutic agents which are effective in the treatment thereof. Such agents prolong the survival of the patient, inhibit the rapidly-proliferating cell growth associated with the neoplasm, or effect a regression of the neoplasm.

HDAC inhibitors (HDACi) are an emerging class of therapeutic agents that promote differentiation and apoptosis in hematologic and solid malignancies through chromatin remodeling and gene expression regulation. Although the antitumor effects of HDACi have been studied, the impact of HDACi on cancer patient systemic immunity remains unclear.

There is a need for cancer immunotherapy in multiple indications, e.g., non-small cell lung cancer, melanoma, etc. Accordingly, a significant need exists in the art for efficacious compounds, compositions, and methods useful in the treatment of cancer, alone or in conjunction with other therapies used to treat these diseases and conditions. The present invention is directed to meeting this need.

SUMMARY

Provided herein as such in one embodiment is a method of selecting a patient for combination therapy comprising an HDAC inhibitor and a second therapeutic agent comprising: providing a peripheral blood sample from the patient, wherein the patient is diagnosed with a cancer; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to total live peripheral blood mononuclear cells is greater than a pre-determined percentage.

Provided herein as such in one embodiment is a method of selecting a patient for combination therapy comprising an HDAC inhibitor and a second therapeutic agent comprising: providing a peripheral blood sample from the patient, wherein the patient is diagnosed with a cancer, e.g., non-small cell lung cancer and/or melanoma; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to total live peripheral blood mononuclear cells is greater than a pre-determined percentage.

Provided herein as such in one embodiment is a method of selecting a patient for combination therapy comprising an HDAC inhibitor and a second therapeutic agent comprising: providing a peripheral blood sample from the patient, wherein the patient is diagnosed with a cancer and progressed on and/or was considered unresponsive to prior therapy; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to total live peripheral blood mononuclear cells is greater than a pre-determined percentage.

Provided herein as such in one embodiment is a method of selecting a patient for combination therapy comprising an HDAC inhibitor and a second therapeutic agent comprising: providing a peripheral blood sample from the patient, wherein the patient is diagnosed with a diagnosed with a cancer, e.g., non-small cell lung cancer and/or melanoma and progressed on and/or was considered unresponsive to prior therapy; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to total live peripheral blood mononuclear cells is greater than a pre-determined percentage.

Provided herein as such in one embodiment is a method of providing a prognosis for cancer in a patient comprising: providing a peripheral blood sample from the patient, wherein the patient is diagnosed with a cancer; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to total live peripheral blood mononuclear cells is greater than a pre-determined percentage.

Provided herein as such in one embodiment is a method of providing a prognosis for cancer in a patient comprising: providing a peripheral blood sample from the patient, wherein the patient is diagnosed with a cancer, e.g., non-small cell lung cancer and/or melanoma; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to total live peripheral blood mononuclear cells is greater than a pre-determined percentage.

Provided herein as such in one embodiment is a method of providing a prognosis for cancer in a patient comprising: providing a peripheral blood sample from the patient, wherein the patient is diagnosed with a cancer and progressed on and/or was considered unresponsive to prior therapy; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to total live peripheral blood mononuclear cells is greater than a pre-determined percentage.

Provided herein as such in one embodiment is a method of providing a prognosis for cancer in a patient comprising: providing a peripheral blood sample from the patient, wherein the patient is diagnosed with a diagnosed with non-small cell lung cancer and/or melanoma and progressed on and/or was considered unresponsive to prior therapy; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to total live peripheral blood mononuclear cells is greater than a pre-determined percentage.

Provided herein as such in one embodiment is a method of selecting a patient for combination therapy comprising an HDAC inhibitor and a second therapeutic agent comprising: providing a peripheral blood sample from the patient, wherein the patient is diagnosed with a cancer; measuring the number of cells in the peripheral blood sample CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to live peripheral blood mononuclear cells is greater than about at least 5%, such as about at least 20%.

Provided herein as such in one embodiment is a method of selecting a patient for combination therapy comprising an HDAC inhibitor and a second therapeutic agent comprising: providing a peripheral blood sample from the patient, wherein the patient is diagnosed with a cancer, e.g., non-small cell lung cancer and/or melanoma; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to live peripheral blood mononuclear cells is greater than about at least 5%, such as about at least 20%.

Provided herein as such in one embodiment is a method of selecting a patient for combination therapy comprising an HDAC inhibitor and a second therapeutic agent comprising: providing a peripheral blood sample from the patient, wherein the patient is diagnosed with a cancer and progressed on and/or was considered unresponsive to prior therapy; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to live peripheral blood mononuclear cells is greater than about at least 5%, such as about at least 20%.

Provided herein as such in one embodiment is a method of selecting a patient for combination therapy comprising an HDAC inhibitor and a second therapeutic agent comprising: providing a peripheral blood sample from the patient, wherein the patient is diagnosed with a diagnosed with a cancer, e.g., non-small cell lung cancer and/or melanoma and progressed on and/or was considered unresponsive to prior therapy; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to live peripheral blood mononuclear cells is greater than about at least 5%, such as about at least 20%.

Provided herein as such in one embodiment is a method of providing a prognosis for cancer in a patient comprising: providing a peripheral blood sample from the patient, wherein the patient is diagnosed with a cancer; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to total live peripheral blood mononuclear cells is greater than about at least 5%, such as about at least 20%.

Provided herein as such in one embodiment is a method of providing a prognosis for cancer in a patient comprising: providing a peripheral blood sample from the patient, wherein the patient is diagnosed with a cancer, wherein the patient is diagnosed with a cancer, e.g., non-small cell lung cancer and/or melanoma; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to total live peripheral blood mononuclear cells is greater than about at least 5%, such as about at least 20%.

Provided herein as such in one embodiment is a method of providing a prognosis for cancer in a patient comprising: providing a peripheral blood sample from the patient, wherein the patient is diagnosed with a cancer and or progressed on and/or was considered unresponsive to prior therapy; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to total live peripheral blood mononuclear cells is greater than about at least 5%, such as about at least 20%.

Provided herein as such in one embodiment is a method of providing a prognosis for cancer in a patient comprising: providing a peripheral blood sample from the patient, wherein the patient is diagnosed with a diagnosed with a cancer, e.g., non-small cell lung cancer and/or melanoma and progressed on and/or was considered unresponsive to prior therapy; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16- negative cells relative to total live peripheral blood mononuclear cells is greater than about at least 5%, such as about at least 20%.

Provided herein as such in one embodiment is a method of selecting a patient for combination therapy comprising entinostat and a second therapeutic agent comprising: providing a peripheral blood sample from the patient, wherein the patient is diagnosed with a cancer; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to live peripheral blood mononuclear cells is greater than about at least 5%, such as about at least 20%.

Provided herein as such in one embodiment is a method of selecting a patient for combination therapy comprising entinostat and a second therapeutic agent comprising: providing a peripheral blood sample from the patient, wherein the patient is diagnosed with a cancer, e.g., non-small cell lung cancer and/or melanoma; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to live peripheral blood mononuclear cells is greater than about at least 5%, such as about at least 20%.

Provided herein as such in one embodiment is a method of selecting a patient for combination therapy comprising entinostat and a second therapeutic agent comprising: providing a peripheral blood sample from the patient, wherein the patient is diagnosed with a cancer and progressed on and/or was considered unresponsive to prior therapy; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to live peripheral blood mononuclear cells is greater than about at least 5%, such as about at least 20%.

Provided herein as such in one embodiment is a method of selecting a patient for combination therapy comprising entinostat and a second therapeutic agent comprising: providing a peripheral blood sample from the patient, wherein the patient is diagnosed with a cancer, e.g., non-small cell lung cancer and/or melanoma and progressed on and/or was considered unresponsive to prior therapy; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to live peripheral blood mononuclear cells is greater than about at least 5%, such as about at least 20%.

Provided herein as such in one embodiment is a method of selecting a patient for combination therapy comprising entinostat and an anti-PD-1 antibody comprising: providing a peripheral blood sample from the patient, wherein the patient is diagnosed with a cancer; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to live peripheral blood mononuclear cells is greater than about at least 5%, such as about at least 20%.

Provided herein as such in one embodiment is a method of selecting a patient for combination therapy comprising entinostat and an anti-PD-1 antibody comprising: providing a peripheral blood sample from the patient, wherein the patient is diagnosed with a cancer, e.g., non-small cell lung cancer and/or melanoma; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to live peripheral blood mononuclear cells is greater than about at least 5%, such as about at least 20%.

Provided herein as such in one embodiment is a method of selecting a patient for combination therapy comprising entinostat and an anti-PD-1 antibody comprising: providing a peripheral blood sample from the patient, wherein the patient is diagnosed with a cancer and progressed on and/or was considered unresponsive to prior therapy; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to live peripheral blood mononuclear cells is greater than about at least 5%, such as about at least 20%.

Provided herein as such in one embodiment is a method of selecting a patient for combination therapy comprising entinostat and an anti-PD-1 antibody comprising: providing a peripheral blood sample from the patient, wherein the patient is diagnosed with a cancer, e.g., non-small cell lung cancer and/or melanoma and progressed on and/or was considered unresponsive to prior therapy; measuring the number of cells in the peripheral blood sample which are CD14-positive, HLA-DR-high, and/or CD16-negative; measuring the number of total peripheral blood mononuclear cells in the peripheral blood sample; and administering a combination therapy if the percentage of CD14-positive, HLA-DR-high, and/or CD16-negative cells relative to live peripheral blood mononuclear cells is greater than about at least 5%, such as about at least 20%.

In some embodiments, the anti-PD-1 antibody, the anti-PD-L1 and/or the CTLA4-blocking therapeutic and the HDAC inhibitor are administered in temporal proximity for treating cancer. In some embodiments, the disclosure provides a synergistic composition of the anti-PD-1 antibody, the anti-PD-L1 and/or the CTLA4-blocking therapeutic and the HDAC inhibitor, wherein the anti-PD-1 antibody, the anti-PD-L1 antibody and/or the CTLA4-blocking therapeutic and the HDAC inhibitor and come into contact with each other in the human body (e.g., only in the human body).

In some embodiments, the disclosure provides a method of preparing a composition by bringing the anti-PD-1 antibody, the anti-PD-L1 and/or the CTLA4-blocking therapeutic and the HDAC inhibitor into contact with each other at a locus.

DETAILED DESCRIPTION

Figure 1:
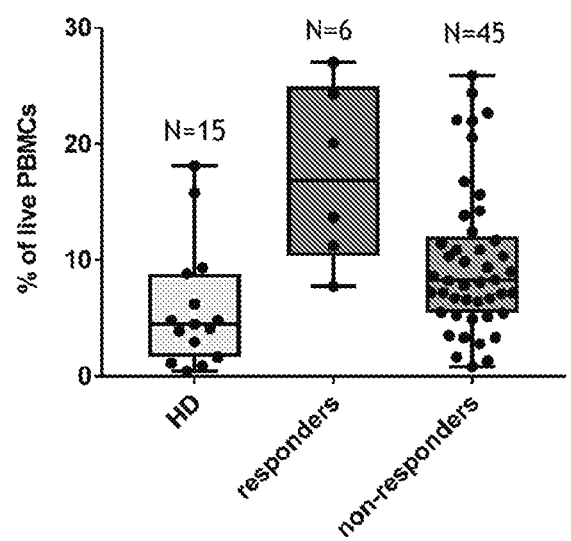
FIG. 1 illustrates the percentage of CD14+HLA-DR$^{Hi}$CD16− monocyte cells with respect to total live PBMCs in blood samples obtained from pre-treatment donors, grouped into one of three categories: healthy donors (HD), NSCLC patients responding to combination treatment (responders), and NSCLC patients not responding to combination treatment (non-responders), showing the predictive and prognostic significance of baseline, pre-treatment CD14+HLA-DR$^{Hi}$CD16− cell percentage relative to total peripheral blood mononuclear cells.
Figure 2:
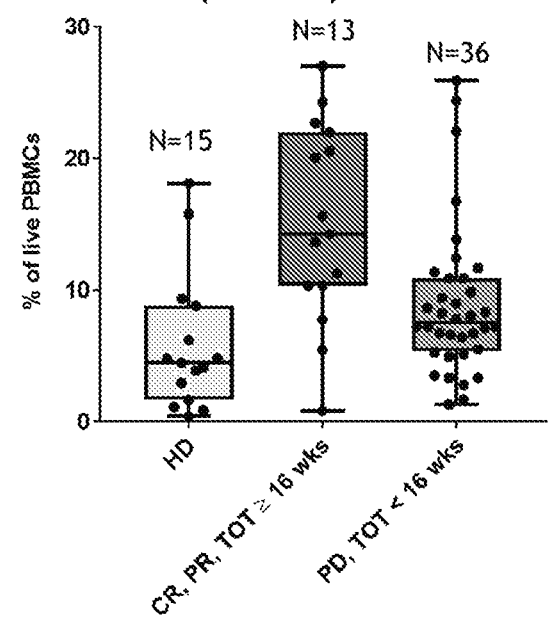
FIG. 2 illustrates the percentage of CD14+HLA-DR$^{Hi}$CD16− monocyte cells with respect to total live PBMCs in blood samples obtained from pre-treatment donors, grouped into one of three categories: (1) healthy donors (HD), (2) NSCLC patients having an objective response to combination treatment (complete response (CR) and partial response (PR)) merged with patients with time on treatment (TOT)≥16 weeks, and (3) progressive disease (PD) merged with patients with time on treatment <16 weeks, showing the predictive and prognostic significance of baseline, pre-treatment CD14+HLA-DR$^{Hi}$CD16− cell percentage relative to total peripheral blood mononuclear cells.
Figure 3:
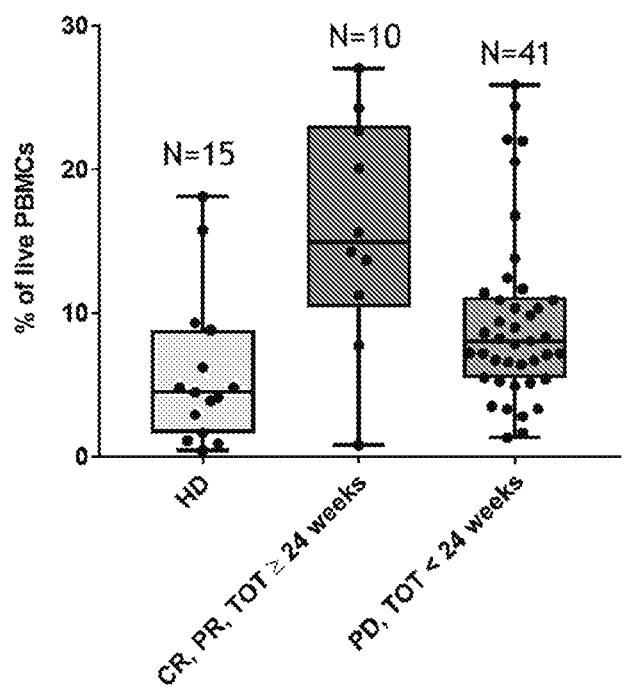
FIG. 3 illustrates the percentage of CD14+HLA-DR$^{Hi}$CD16− monocyte cells with respect to total live PBMCs in blood samples obtained from pre-treatment donors, grouped into one of three categories: (1) healthy donors (HD), (2) NSCLC patients having an objective response to combination treatment (complete response (CR) and partial response (PR)) merged with patients with time on treatment (TOT)≥24 weeks, and (3) progressive disease (PD) merged with patients with time on treatment <24 weeks, showing the predictive and prognostic significance of baseline, pre-treatment CD14+HLA-DR$^{Hi}$CD16− cell percentage relative to total peripheral blood mononuclear cells.
Figure 4:
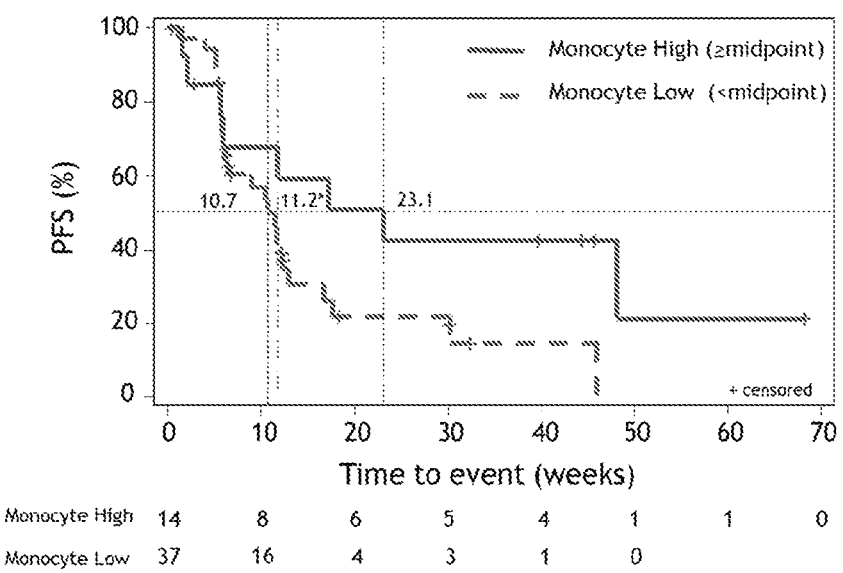
FIG. 4 illustrates the percentage of NSCLC patients who remained progression free (progression free survival (PFS)) at particular time intervals. Patients were grouped according to their baseline CD14+HLA-DR$^{Hi}$CD16− monocyte cell percentage relative to total peripheral blood mononuclear cells falling above/equal to or below a calculated midpoint monocyte percentage of 13.1% of total peripheral blood mononuclear cells.
Figure 5:
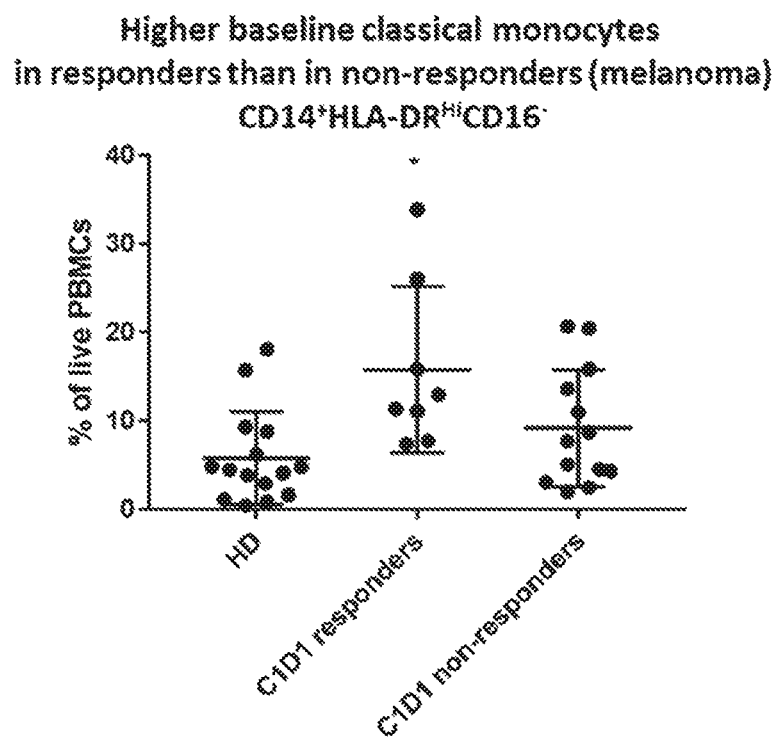
FIG. 5 illustrates the percentage of CD14+HLA-DR$^{Hi}$CD16− monocyte cells with respect to total live PBMCs in blood samples obtained from donors on the first day of the first cycle (C1D1) of treatment, grouped into one of three categories: healthy donors (HD), melanoma patients responding to combination treatment (C1D1 responders), and melanoma patients not responding to combination treatment (C1D1 non-responders), showing the predictive and prognostic significance of baseline, pre-treatment CD14+HLA-DR$^{Hi}$CD16− cell percentage relative to total peripheral blood mononuclear cells.
Figure 6:
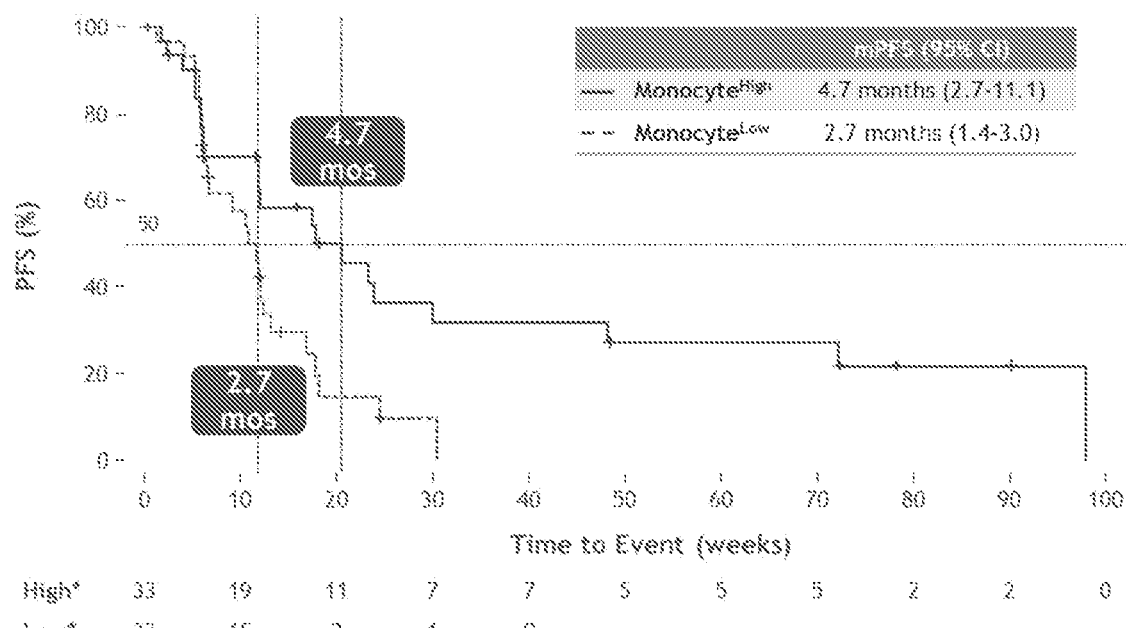
FIG. 6 illustrates the percentage of NSCLC patients who remained progression free (progression free survival (PFS)) at particular time intervals. Patients were grouped according to their baseline CD14+HLA-DR$^{Hi}$CD16− monocyte cell percentage relative to total peripheral blood mononuclear cells falling above/equal to or below a calculated midpoint monocyte percentage of 9% of total live peripheral blood mononuclear cells. Data shows that patients with hih levels of monocyte at baseline experiences a significantly longer PFS benefit from the combination therapy.
Figure 7:
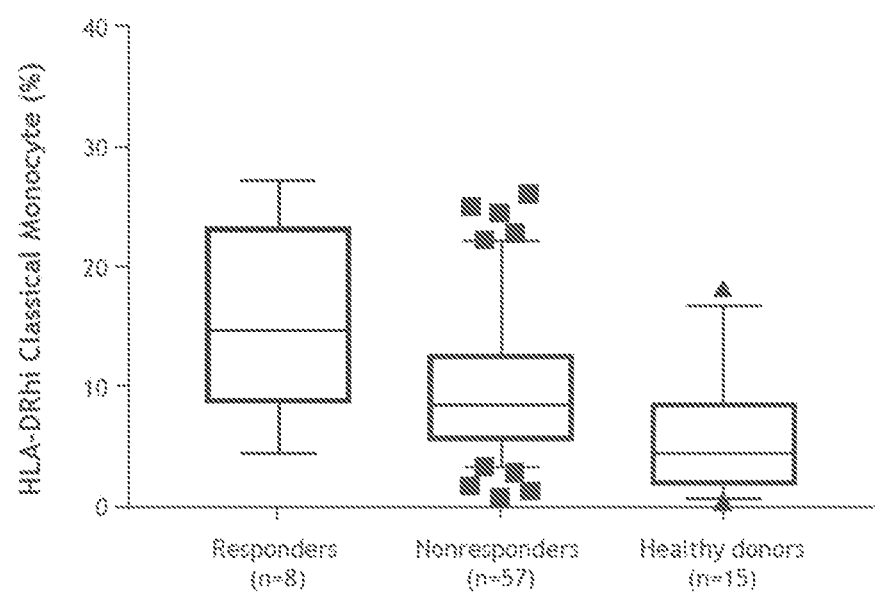
FIG. 7 illustrates the percentage of CD14+HLA-DR$^{Hi}$CD16− monocyte cells with respect to total live PBMCs in blood samples obtained from pre-treatment donors, grouped into one of three categories: (1) healthy donors, (2) NSCLC patients responding to combination treatment, and (3) non-responders, showing the predictive and prognostic significance of baseline, pre-treatment CD14+HLA-DR$^{Hi}$CD16− cell percentage relative to total peripheral blood mononuclear cells.
Figure 8:
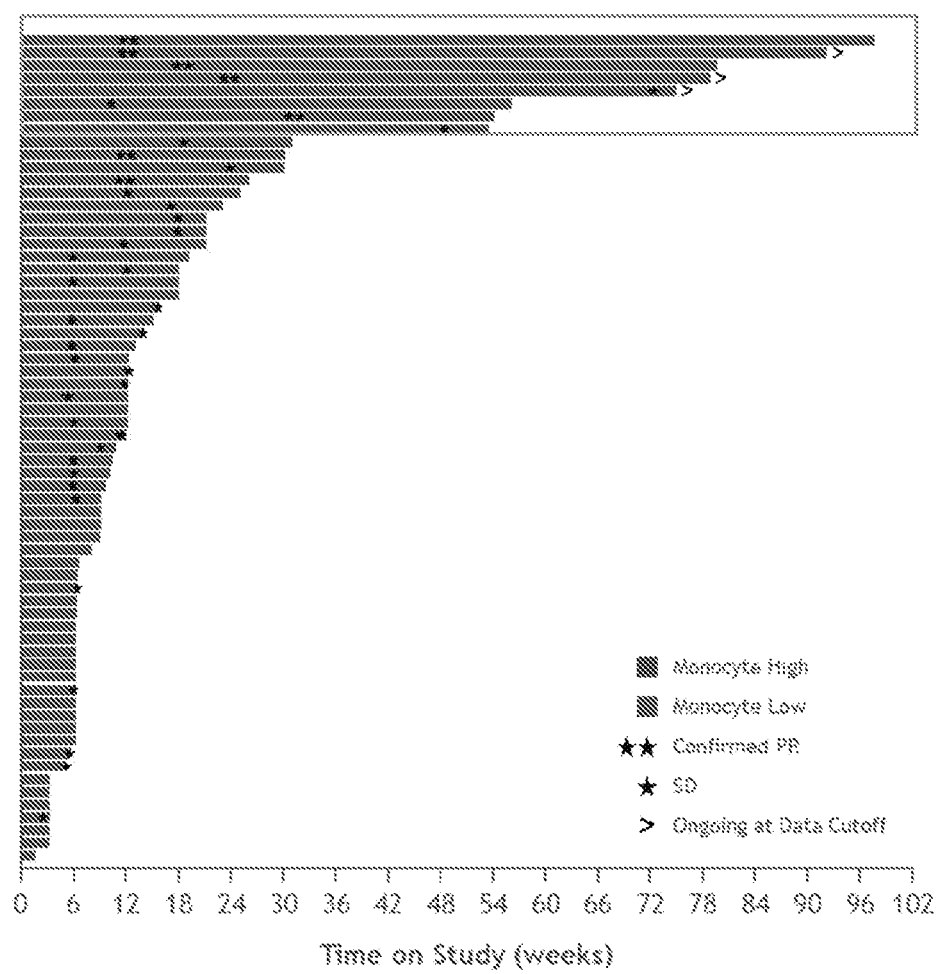
FIG. 8 illustrates the patients with high monocytes, low monocytes, a confirmed partial response or a stable disease during the study showing that responders with high baseline monocytes also experienced enhanced durability.

Conventional approaches for selecting cancer patients for combination therapy rely upon assessment of the cancer, either in terms of histology or molecular analyses. The present disclosure provides methods that rely upon the levels of peripheral blood mononuclear cells which are CD14-positive, HLA-DR-high, and/or CD16-negative in a biological sample obtained from a cancer patient as a predictive and prognostic biomarker for selecting a patient for a combination therapy with an HDAC inhibitor and a second therapeutic agent.

Provided herein as such in one embodiment is a method of selecting a patient for combination therapy comprising an HDAC inhibitor and a second therapeutic agent comprising: obtaining a peripheral blood sample from the patient, wherein the patient is diagnosed with a cancer; measuring the number of cells in the peripheral blood sample which are CD14-positive, HLA-DR-high, and/or CD16-negative; measuring the number of total peripheral blood mononuclear cells in the peripheral blood sample; and administering the combination therapy if the percentage of the CD14-positive, HLA-DR-high, and/or CD16-negative cells is greater than between 5% and 40%.

Provided herein as such in one embodiment is a method of selecting a patient for combination therapy comprising an HDAC inhibitor and a second therapeutic agent comprising: obtaining a peripheral blood sample from the patient, wherein the patient is diagnosed with a cancer; measuring the number of cells in the peripheral blood sample which are CD14-positive, HLA-DR-high, and/or CD16-negative; measuring the number of total peripheral blood mononuclear cells in the peripheral blood sample; and administering the combination therapy if the percentage of the CD14-positive, HLA-DR-high, and/or CD16-negative cells is greater than 5%.

Provided herein as such in one embodiment is a method of selecting a patient for combination therapy comprising an HDAC inhibitor and a second therapeutic agent comprising: obtaining a peripheral blood sample from the patient, wherein the patient is diagnosed with a cancer; measuring the number of cells in the peripheral blood sample which are CD14-positive, HLA-DR-high, and/or CD16-negative; measuring the number of total peripheral blood mononuclear cells in the peripheral blood sample; and administering the combination therapy if the percentage of the CD14-positive, HLA-DR-high, and/or CD16-negative cells is greater than 10%.

Provided herein as such in one embodiment is a method of selecting a patient for combination therapy comprising an HDAC inhibitor and a second therapeutic agent comprising: obtaining a peripheral blood sample from the patient, wherein the patient is diagnosed with a cancer; measuring the number of cells in the peripheral blood sample which are CD14-positive, HLA-DR-high, and/or CD16-negative; measuring the number of total peripheral blood mononuclear cells in the peripheral blood sample; and administering the combination therapy if the percentage of the CD14-positive, HLA-DR-high, and/or CD16– negative cells is greater than 15%.

Provided herein as such in one embodiment is a method of selecting a patient for combination therapy comprising an HDAC inhibitor and a second therapeutic agent comprising: obtaining a peripheral blood sample from the patient, wherein the patient is diagnosed with a cancer; measuring the number of cells in the peripheral blood sample which are CD14-positive, HLA-DR-high, and/or CD16-negative; measuring the number of total peripheral blood mononuclear cells in the peripheral blood sample; and administering the combination therapy if the percentage of the CD14-positive, HLA-DR-high, and/or CD16-negative cells is greater than 20%.

Provided herein as such in one embodiment is a method of selecting a patient for combination therapy comprising an HDAC inhibitor and a second therapeutic agent comprising: obtaining a peripheral blood sample from the patient, wherein the patient is diagnosed with a cancer; measuring the number of cells in the peripheral blood sample which are CD14-positive, HLA-DR-high, and/or CD16-negative; measuring the number of total peripheral blood mononuclear cells in the peripheral blood sample; and administering the combination therapy if the percentage of the CD14-positive, HLA-DR-high, and/or CD16-negative cells is greater than about 25%.

Provided herein as such in one embodiment is a method of selecting a patient for combination therapy comprising an HDAC inhibitor and a second therapeutic agent comprising: obtaining a peripheral blood sample from the patient, wherein the patient is diagnosed with a cancer; measuring the number of cells in the peripheral blood sample which are CD14-positive, HLA-DR-high, and/or CD16-negative; measuring the number of total peripheral blood mononuclear cells in the peripheral blood sample; and administering the combination therapy if the percentage of the CD14-positive, HLA-DR-high, and/or CD16-negative cells is greater than about 30%.

In some embodiments, the peripheral blood sample is treated with an anticoagulant.

In some embodiments, the patient diagnosed with a cancer had previously received treatment. In some embodiments, the patient diagnosed with a cancer had previously received treatment and progressed. In some embodiments, the patient diagnosed with a cancer had previously received treatment and was found unresponsive. In some embodiments, the previously received treatment is selected from anti-PD-1, anti-PD-L1, and CTLA4-blocking treatment. In some embodiments, the patient diagnosed with a cancer had never received treatment.

In some embodiments, measuring number of cells in the peripheral blood sample which are CD14-positive, HLA-DR-high, and/or CD16-negative cells is performed by flow cytometry. In some embodiments, the peripheral blood mononuclear cell population is identified by a cell surface marker. In some embodiments, the percentage of CD14-positive, HLA-DR-high, and/or CD16-negative cells relative to total PBMCs is between at least about 1% and 100%. In some embodiments, the percentage of the CD14-positive, HLA-DR-high, and/or CD16-negative cells relative to total PBMCs is between at least about 5% and 100%. In some embodiments, the percentage of the CD14-positive, HLA-DR-high, and/or CD16-negative cells relative to total PBMCs is between at least about 10% and 100%. In some embodiments, the percentage of the CD14-positive, HLA-DR-high, and/or CD16-negative cells relative to total PBMCs is between at least about 15% and 100%. In some embodiments, the percentage of the CD14-positive, HLA-DR-high, and/or CD16-negative cells is between at least about 20% and 100%. In some embodiments, the percentage of the CD14-positive, HLA-DR-high, and/or CD16-negative cells is between at least about 25% and 100%. In some embodiments, the percentage of the CD14-positive, HLA-DR-high, and/or CD16-negative cells is between at least about 30% and 100%. In some embodiments, the percentage of the CD14-positive, HLA-DR-high, and/or CD16-negative cells is between at least about 35% and 100%. In some embodiments, the percentage of the CD14-positive, HLA-DR-high, and/or CD16-negative cells is between 40% and 100%.

In some embodiments, the HDAC inhibitor is entinostat. In some embodiments, the HDAC inhibitor is vorinostat (SAHA). In some embodiments, the HDAC inhibitor is valproic acid. In some embodiments, the HDAC inhibitor is selected from belinostat (PXD101), LAQ824, panobinostat (LBH589), CI994, chidamide (HBI-8000; Epidaza®) and mocetinostat (MGCD0103).

In some embodiments, the HDAC inhibitor is administered orally. In some embodiments, the HDAC inhibitor is administered first. In some embodiments, the HDAC inhibitor is administered weekly. In some embodiments, the HDAC inhibitor is administered every two weeks.

In some embodiments, the second therapeutic agent is an anti-PD-1 antibody. In some embodiments, the anti-PD-1 antibody is pembrolizumab. In some embodiments, the anti-PD-1 antibody is nivolumab. In some embodiments, the cancer is a lung cancer. In some embodiments, the lung cancer is a non-small cell lung cancer, squamous cell carcinoma, or large cell carcinoma. In some embodiments, the cancer is a melanoma. In some embodiments, the melanoma is a metastatic melanoma.

In some embodiments, the second therapeutic agent is an anti-PD-L1 antibody. In some embodiments, the anti-PD-L1 antibody is MPDL3280A. In some embodiments, the anti-PD-L1 antibody is avelumab. In some embodiments, the anti-PD-L1 antibody is durvalumab. In some embodiments, the second therapeutic agent is MPDL3280A and the breast cancer is a triple-negative breast cancer.

In some embodiments, the anti-PD-1 antibody or anti-PD-L1 antibody is administered by infusion.

In some embodiments, the second therapeutic agent is a CTLA4-blocking agent. In some embodiments, the CTLA4-blocking agent is ipilimumab. In some embodiments, the CTLA4-blocking agent is tremelimumab.

To facilitate understanding of the disclosure set forth herein, a number of terms are defined below.

As used herein, "progression," refers to a disease, such as cancer, wherein the condition has worsened or has spread throughout the body.

As used herein, the phrases "unresponsive to" and "did not respond to" refer to a patient or condition that was treated and the treatment was not effective in one or both of preventing the progression or reversing the course of the disease.

As used herein, "abnormal cell growth," refers to cell growth that is independent of normal regulatory mechanisms (e.g., loss of contact inhibition), including the abnormal growth of normal cells and the growth of abnormal cells.

"Neoplasia" as described herein, is an abnormal, unregulated and disorganized proliferation of cells that is distinguished from normal cells by autonomous growth and somatic mutations. As neoplastic cells grow and divide they pass on their genetic mutations and proliferative characteristics to progeny cells. A neoplasm, or tumor, is an accumulation of neoplastic cells. In some embodiments, the neoplasm can be benign or malignant.

"Metastasis," as used herein, refers to the dissemination of tumor cells via lymphatics or blood vessels. Metastasis also refers to the migration of tumor cells by direct extension through serous cavities, or subarachnoid or other spaces. Through the process of metastasis, tumor cell migration to other areas of the body establishes neoplasms in areas away from the site of initial appearance.

As discussed herein, "angiogenesis" is prominent in tumor formation and metastasis. Angiogenic factors have been found associated with several solid tumors such as rhabdomyosarcomas, retinoblastoma, Ewing sarcoma, neuroblastoma, and osteosarcoma. A tumor cannot expand without a blood supply to provide nutrients and remove cellular wastes. Tumors in which angiogenesis is important include solid tumors such as renal cell carcinoma, hepatocellular carcinoma, and benign tumors such as acoustic neuroma, and neurofibroma. Angiogenesis has been associated with blood-born tumors such as leukemias. It is believed that angiogenesis plays a role in the abnormalities in the bone marrow that give rise to leukemia. Prevention of angiogenesis could halt the growth of cancerous tumors and the resultant damage to the subject due to the presence of the tumor.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The terms "treat," "treating," and "treatment" are meant to include alleviating or abrogating a disorder, disease, or condition; or one or more of the symptoms associated with the disorder, disease, or condition; or alleviating or eradicating the cause(s) of the disorder, disease, or condition itself.

The term "therapeutically effective amount" refers to the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a cell, tissue, system, animal, or human that is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy*, 21st Edition; Lippincott Williams & Wilkins: Philadelphia, Pa., 2005; *Handbook of Pharmaceutical Excipients*, 5th Edition; Rowe et al., Eds., The Pharmaceutical Press and the American Pharmaceutical Association: 2005; and *Handbook of Pharmaceutical Additives*, 3rd Edition; Ash and Ash Eds., Gower Publishing Company: 2007; *Pharmaceutical Preformulation and Formulation*, Gibson Ed., CRC Press LLC: Boca Raton, Fla., 2004).

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "high", when used to describe expression of a cell surface marker on a cell, corresponds to an elevated level of expression of the cell surface marker on the cell relative to a control cell. A high level of expression can be about a 10-fold increase, about a 100-fold increase, about a 1000-fold increase, about a 10000-fold increase, about a 20-fold increase, about a 200-fold increase, about a 2000-fold increase, about a 20000-fold increase, about a 30-fold increase, about a 300-fold increase, about a 3000-fold increase, about a 30000-fold increase, about a 40-fold increase, about a 400-fold increase, about a 4000-fold increase, about a 40000-fold increase, about a 50-fold increase, about a 500-fold increase, about a 5000-fold increase, about a 50000-fold increase, about a 60-fold increase, about a 600-fold increase, about a 6000-fold increase, about a 60000-fold increase, about a 70-fold increase, about a 700-fold increase, about a 7000-fold increase, about a 70000-fold increase, about a 80-fold increase, about a 800-fold increase, about a 8000-fold increase, about a 80000-fold increase, about a 90-fold increase, about a 2900-fold increase, about a 9000-fold increase, about a 90000-fold increase, relative to an unstained control cell.

A "high" level of expression can be from about a 10-fold increase to about a 100-fold increase, from about a 100-fold increase to about a 1000-fold increase, from about a 20-fold increase to about a 200-fold increase, from about a 200-fold increase to about a 2000-fold increase, from about a 30-fold increase to about a 300-fold increase, from about a 300-fold increase to about a 3000-fold increase, from about a 40-fold increase to about a 400-fold increase, from about a 400-fold increase to about a 4000-fold increase, from about a 50-fold increase to about a 500-fold increase, from about a 500-fold increase to about a 5000-fold increase, from about a 60-fold increase to about a 600-fold increase, from about a 600-fold increase to about a 6000-fold increase, from about a 70-fold increase to about a 700-fold increase, from about a 700-fold increase to about a 7000-fold increase, from about a 80-fold increase to about a 800-fold increase, from about a 800-fold increase to about a 8000-fold increase, from about a 90-fold increase to about a 9300-fold increase, from about a 900-fold increase to about a 9000-fold increase, relative to an unstained control cell.

A high level of expression can be from about a 1 order of magnitude ($10^1$) increase, from about a 2 orders of magnitude ($10^2$) increase, from about a 3 orders of magnitude ($10^3$) increase, from about a 4 orders of magnitude ($10^4$) increase, from about a 5 orders of magnitude ($10^5$) increase, relative to an unstained control cell.

Cancer, tumors, tumor-related disorders, and neoplastic disease states are serious and often times life-threatening conditions. These diseases and disorders, which are characterized by rapidly-proliferating cell growth, continue to be the subject of research efforts directed toward the identification of therapeutic agents which are effective in the treatment thereof. Such agents prolong the survival of the patient, inhibit the rapidly-proliferating cell growth associated with the neoplasm, or effect a regression of the neoplasm.

HDAC Inhibitors

HDAC inhibitors are an emerging class of therapeutic agents that promote differentiation and apoptosis in hematologic and solid malignancies through chromatin remodeling and gene expression regulation. HDAC inhibitors can be classified broadly into pan HDAC inhibitors and selective HDAC inhibitors. Although there is a large structural diversity of known HDAC inhibitors, they share common features: a part that interacts with the enzyme active site and a side-chain that sits inside the channel leading to the active site. This can be seen with the hydroxamates such as SAHA, where the hydroxamate group is believed to interact with the active site. In the case of the depsipeptides, it is believed that an intracellular reduction of the disulphide bond creates a free thiol group (which interacts with the active site) attached to a 4-carbon alkenyl chain. A difference between the HDAC inhibitors is in the way that they interact with the rim of the HDAC channel, which is at the opposite end of the channel to the active site. It is this interaction, between the HDAC inhibitor and the rim of the channel, which is believed to account, at least in part, for some observed differences in HDAC selectivity between pan-HDAC inhibitors, such as SAHA and selective HDAC inhibitors such as the depsipeptides.

Several HDAC inhibitors have been identified including benzamides (entinostat), short-chain fatty acids (i.e., Sodium phenylbutyrate); hydroxamic acids (i.e., suberoylanilide hydroxamic acid and thrichostatin A); cyclic tetrapeptides containing a 2-amino-8-oxo-9, 10-epoxy-decanoyl moiety (i.e., trapoxin A) and cyclic peptides without the 2-amino-8-oxo-9, 10-epoxy-decanoyl moiety (i.e., FK228). A particularly preferred HDAC inhibitor is entinostat. Entinostat has the chemical name N-(2-aminophenyl)-4-[N-(pyridine-3-yl)methoxycarbonylamino-methyl]-benzamide and the chemical structure shown below.

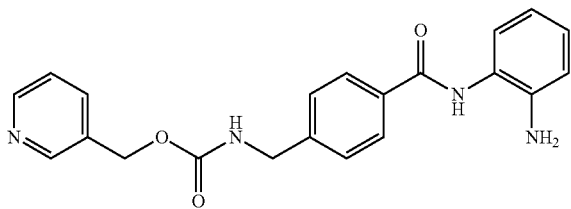 [SMILES: Nc1ccccc1NC(=O)c1ccc(CNC(=O)OCc2cccnc2)cc1]

Entinostat is a benzamide HDAC inhibitor undergoing clinical investigation in multiple types of solid tumors and hematologic cancers. Entinostat is rapidly absorbed and has a half-life of about 100 hours and, importantly, changes in histone acetylation persist for several weeks following the administration of entinostat.

Entinostat, a class I HDAC inhibitor, has shown promising activity. Emerging preclinical work suggests that entinostat has immunomodulatory effects on immune suppressor cells including regulatory T cells (Tregs) and myeloid derived suppressor cells (MDSCs) and can eradicate modestly immunogenic mouse tumors in combination with immune checkpoint blockade agents. This activity was shown to be mediated via reduction of MSDCs (Kim et al., PNAS 2014, 111:11774-9). These results may be explained by entinostat's selective targeting of those class 1 HDAC enzymes which have been shown to play a role in the differentiation and activation of Tregs (Shen et al. PLoS One 2012, 7:e30815; Wang et al. JCI 2015, 125:1111-1123) and MDSCs (Youn et al. Nat. Immunol 2013, 14:211-220).

The methods and results are also described in Tomita et al., "The interplay of epigenetic therapy and immunity in locally recurrent or metastatic estrogen receptor-positive breast cancer: Correlative analysis of ENCORE 301, a randomized, placebo-controlled phase II trial of exemestane with or without entinostat", *ONCOIMMUNOLOGY*, Taylor and Francis Online, 2016, the entire contents of which are hereby incorporated by reference in its entirety.

In summary, data from blood samples obtained from ER+ breast cancer patients treated with entinostat combined with exemestane in ENCORE 301 provided the first evidence of HDACi-mediated reduction of immunosuppressive MDSCs and increased immunocompetent CD14+HLA-DR$^{Hi}$ monocytes in patients. These findings may in part explain the improved overall survival and provide strong rationale for planned combination studies of entinostat with immune checkpoint blockade.

The reduction in MDSCs in entinostat treated patients was consistent with recently published preclinical work (Kim et al PNAS 2014) demonstrating entinostat's ability to enhance the anti-tumor activity of immune checkpoint inhibitors through reduction of MDSCs.

Recent advances in immunotherapy highlight the antitumor effects of immune checkpoint inhibition. Entinostat displays immunomodulatory activity including the targeting of immune suppressor cells in the tumor microenvironment as described in Orillion et al., "Entinostat Neutralizes Myeloid-Derived Suppressor Cells and Enhances the Antitumor Effect of PD-1 Inhibition in Murine Models of Lung and Renal Cell Carcinoma", *Clinical Cancer Research*, American Association for Cancer Research, 23(2017); pages 5187-5201, the entire contents of which are hereby incorporated by reference in its entirety. It was found that entinostat enhanced the antitumor effect of PD-1 inhibition in two syngeneic mouse tumor models by reducing tumor growth and increasing survival.

Histone Deacetylases

The HDACs are a family including at least eighteen enzymes, grouped in three classes (Class I, II and III). Class I HDACs include, but are not limited to, HDACs 1, 2, 3, and 8. Class I HDACs can be found in the nucleus and are believed to be involved with transcriptional control repressors. Class II HDACs include, but are not limited to, HDACS 4, 5, 6, 7, and 9 and can be found in both the cytoplasm as well as the nucleus. Class III HDACs are believed to be NAD dependent proteins and include, but are not limited to, members of the Sirtuin family of proteins. Non-limiting examples of sirtuin proteins include SIRT1-7. As used herein, the term "selective HDAC" refers to an HDAC inhibitor that does not interact with all three HDAC classes.

Programmed Cell Death-1 (PD-1)

PD-1 is a cell surface receptor that is a member of the CD28 family of T-cell regulators, within the immunoglobulin superfamily of receptors. The human PD-1 gene is located at chromosome 2q37, and the full-length PD-1 cDNA encodes a protein with 288 amino acid residues with 60% homology to murine PD-1. It is present on CD4−CD8− (double negative) thymocytes during thymic development and is expressed upon activation in mature hematopoietic cells such as T and B cells, NKT cells and monocytes after prolonged antigen exposure.

Without being bound by any theory, it is contemplated that binding of the ligand PD-L1 to PD-1 downregulates effector anti-tumor T-cell activity and facilitates immune evasion. This is supported by the finding of an association between PD-1/PD-L1 expression and poor prognosis in several tumor types including gastric, ovarian, lung and renal carcinomas. PD-1 has been reported to be predominantly expressed by tumor infiltrating T lymphocytes, in melanoma.

In vitro studies of PD-1 blockade by PD-1-specific antibody showed augmentation of cytotoxic T-cell responses to melanoma-specific antigens including increased frequencies of IFN-γ-secreting antigen-specific cells.

Without being bound by any theory, it is contemplated that targeting PD-1 may act as an effective therapeutic strategy for cancer. The principal method for targeting PD-1 clinically has been through the development of genetically engineered monoclonal antibodies that inhibit either PD-1 or PD-L1 function.

PD-L1 has also been shown to bind to B7-1 (CD80), an interaction that also suppresses T-cell proliferation and cytokine production; however, the exact relative contributions of the PD-L1: PD-1 and PD-L1: B7-1 pathways in cancer remain unclear. The PD-1-targeting agents currently in development inhibit both pathways. However, as the binding sites for PD-1 and B7-1 are adjacent but not overlapping, agents that specifically target one or the other may potentially be developed.

Cancer cells drive high expression levels of PD-L1 on their surface, allowing activation of the inhibitory PD-1 receptor on any T cells that infiltrate the tumor microenvironment, effectively switching those cells off. Indeed, upregulation of PD-L1 expression levels has been demonstrated in many different cancer types (eg, melanoma [40%-100%], NSCLC [35%-95%], and multiple myeloma [93%]), and high levels of PD-L1 expression have been linked to poor clinical outcomes. Furthermore, tumor-infiltrating T cells have been shown to express significantly higher levels of PD-1 than T cells that infiltrate normal tissue. It is thought that the tumor microenvironment may secrete pro-inflammatory cytokines, including interferon-gamma (IFNγ) to upregulate the expression of PD-1 on tumor-infiltrating T cells to ensure that they can respond to the high levels of PD-L1 expressed on the tumor.

Pembrolizumab

Pembrolizumab is a humanized monoclonal IgG4 anti-PD-1 antibody consisting of a high-affinity mouse anti-PD-1-derived variable region grafted on to a human IgG4 immunoglobulin molecule with an engineered Fc region for stabilization. Pre-clinical anti-tumor activity has been demonstrated in animal models of multiple tumor types. A first-in-human, Phase I dose-escalation study was conducted in patients with advanced refractory malignancies at dose levels 1, 3 and 10 mg/kg given intravenously initially and after 4 weeks and then every 2 weeks. The maximum observed toxicity was grade 2 pruritus and no drug-related grade 3 or greater adverse events (AEs) were observed. Therefore, the maximum tolerated dose was not reached. The half-life was 13.6-21.7 days and not obviously dose related. Four patients had some tumor regression. This study was then expanded, with patients receiving pembrolizumab at 10 mg/kg every 2 weeks or either 2 or 10 mg/kg every 3 weeks in non-randomized cohorts; in total, there were 135 patients with melanoma. Enrollment included 48 patients who had received prior ipilimumab but could not have experienced severe immune-related adverse events (irAEs). Though 79% of patients had some AEs, only 13% had severe (grade 3 or 4) drug-related toxicities including skin rash or pruritus, fatigue, diarrhea, abdominal pain and hepatic dysfunction. The highest rate of severe toxicities (23%) was in those receiving the highest dose (10 mg/kg every 2 weeks) versus <10% in the less dose intense cohorts. AEs potentially of an autoimmune nature included isolated instances of pneumonitis, kidney injury, hepatitis, diarrhea, hypothyroidism, hyperthyroidism and adrenal insufficiency. The overall objective response rate (ORR) based on immune-related response criteria was 38% (44 of 117) with 8 additional patients experiencing unconfirmed responses. A total of 77% had some degree of tumor regression including 8 patients with stable disease for over 24 weeks. The majority of responses were established by the time of the first radiologic assessment at 12 weeks. The median progression free survival exceeded 7 months. Biopsies of responding tumors showed dense infiltration by $CD8^+$ T cells.

MPDL3280A

MPDL3280A is a human anti-PD-L1 mAb that contains an engineered fragment crystallizable (Fc) domain designed to optimize efficacy and safety by minimizing antibody-dependent cellular cytotoxicity (ADCC). Without being bound by any specific theory, it is understood that this structure allows inhibition of the PD-1/PD-L1 interaction, while minimizing ADCC-mediated depletion of activated T cells that is required for an effective antitumor immune response.

MPDL3280A has been evaluated in a phase I trial in patients with locally advanced or metastatic solid tumors. A total of 175 patients had been recruited to date. The antibody was administered as a single agent at escalating doses of 51, 3, 10, 15, and 20 mg/kg for a median duration of 127 days. The results of two expansion cohorts have also been reported; a cohort of 85 patients (53 of whom were evaluable for efficacy) with squamous or non-squamous NSCLC and a cohort of 45 metastatic melanoma patients (35 of whom were evaluable for efficacy). In both cohorts doses of 51, 10, 15, and 25 mg/kg MPDL3280A were administered every 3 weeks for up to 1 year. MPDL3280A demonstrated durable responses and was well tolerated; efficacy data are summarized in Table 1. Of the 85 patients in the NSCLC cohort, 55% were heavily pretreated with at least three prior therapies, and 81% were smokers or ex-smokers and 19% were never-smokers. The 24-week PFS rate was 44% in squamous cell NSCLC and 46% in non-squamous cell NSCLC.

Avelumab

Avelumab (MSB0010718C) is a fully human anti-PD-L1 IgG1 antibody currently being investigated in clinical trials. In addition to disruption of immune suppressive signaling induced by the binding of PD-L1 on tumor cells with PD-1 on tumor infiltrating immune cells, avelumab is designed to mediate antibody dependent cellular cytotoxicity (ADCC). The ability of avelumab to induce lysis of human carcinoma cells has been assessed using whole peripheral blood mononuclear cells (PBMCs) or purified natural killer (NK) cells as effectors.

In a recent study (Kwong-Yok Tsang et al., Antibody dependent cellular cytotoxicity activity of a novel anti-PD-L1 antibody, avelumab (MSB0010718C), on human tumor cells, 2015 ASCO Annual Meeting, J Clin Oncol 33, 2015 (suppl; abstr 3038)), using PBMCs as effectors, avelumab was found to induce ADCC in 8 out of 18 human carcinoma cell lines. Furthermore, tumor cell lysis was found to positively correlate with the percentage of PD-L1 positive tumor cells. The percentage of PD-L1 positive tumor cells was reported as mean fluorescence intensity (MFI) determined using flow cytometry. Lysis was increased when NK cells were used as effectors. Pretreating tumor cell lines with IFN-γ increased PD-L1 expression, but augmented lysis in only 4 out of 10 cell lines. Preactivating NK cells with IL-12, however, increased lysis, suggesting a potential for synergy by combining avelumab with IL-12-based therapy. Little or no lysis was observed in NK-mediated ADCC assays vs whole PBMCs or dendritic cells isolated from PBMCs. A tumor cell line insensitive to lysis by CD8+T cells was lysed by ADCC using NK cells and avelumab. In conclusion, the study found that Avelumab induced lysis of many human tumor cell lines via ADCC and further clinical trials are necessary to determine whether the additional mechanism of inducing tumor lysis by ADCC will result in enhanced clinical activity compared with similar agents without ADCC activity.

CTLA4-Blocking Antibodies

Cytotoxic T-lymphocyte-associated antigen 4 (CTLA4) is a T cell surface molecule that was originally identified by differential screening of a murine cytolytic T cell cDNA library. CTLA4 is also a member of the immunoglobulin (Ig) superfamily; CTLA4 comprises a single extracellular Ig domain. CTLA4 transcripts have been found in T cell populations having cytotoxic activity, suggesting that CTLA4 might function in the cytolytic response. Anti-CTLA4 antibodies demonstrate an ability to increase the magnitude of protective immunity in a subject already immunized to protective antigens from a pathogen, e.g., cancer antigens or antigens from an infectious agent. Antibodies against CTLA4 have been described for treating cancer. Specifically, there is increasing interest in the therapeutic benefits of blocking CTLA4 using antagonistic antibodies against CTLA such as ipilimumab (FDA approved for melanoma in 2011) and tremelimumab (not FDA approved) as a means of inhibiting immune system tolerance to tumors and thereby providing a potentially useful immunotherapy strategy for patients with cancer.

Lung Cancer

Lung cancer is the leading cause of cancer deaths in women and men both in the United States and throughout the world. Lung cancer has surpassed breast cancer as the leading cause of cancer deaths in women. In the United States in 2014, 158,040 people were projected to die from lung cancer, which is more than the number of deaths from colon and rectal, breast, and prostate cancer combined. Only about 2% of those diagnosed with lung cancer that has spread to other areas of the body are alive five years after the diagnosis, although the survival rates for lung cancers diagnosed at the earliest stage are higher, with approximately 49% surviving for five years or longer.

Cancer occurs when normal cells undergo a transformation that causes them to grow and multiply without control. The cells form a mass or tumor that differs from the surrounding tissues from which it arises. Tumors are dangerous because they take oxygen, nutrients, and space from healthy cells and because they invade and destroy or reduce the ability of normal tissues to function.

Most lung tumors are malignant. This means that they invade and destroy the healthy tissues around them and can spread throughout the body. The tumors can spread to nearby lymph nodes or through the bloodstream to other organs. This process is called metastasis. When lung cancer metastasizes, the tumor in the lung is called the primary tumor, and the tumors in other parts of the body are called secondary tumors or metastatic tumors.

Some tumors in the lung are metastatic from cancers elsewhere in the body. The lungs are a common site for metastasis. If this is the case, the cancer is not considered to be lung cancer. For example, if prostate cancer spreads via the bloodstream to the lungs, it is metastatic prostate cancer (a secondary cancer) in the lung and is not called lung cancer.

Lung cancer comprises a group of different types of tumors. Lung cancers usually are divided into two main groups that account for about 95% of all cases. The division into groups is based on the type of cells that make up the cancer. The two main types of lung cancer are characterized by the cell size of the tumor when viewed under the microscope. They are called small cell lung cancer (SCLC) and non-small cell lung cancer (NSCLC). NSCLC includes several subtypes of tumors. SCLCs are less common, but they grow more quickly and are more likely to metastasize than NSCLCs. Often, SCLCs have already spread to other parts of the body when the cancer is diagnosed. About 5% of lung cancers are of rare cell types, including carcinoid tumor, lymphoma, and others. As used herein, the term "lung cancer" includes, but is not limited to, SCLC, NSCLC, carcinoid tumor, lymphoma, and their various subtypes.

Non-Small Cell Lung Cancer

NSCLC is a cancer of the lung which is not of the small cell carcinoma (oat cell carcinoma) type. The term "non-small cell lung cancer" applies to the various types of bronchogenic carcinomas (those arising from the lining of the bronchi). Examples of specific types of NSCLC include, but are not limited to, adenocarcinoma, squamous cell carcinoma, and large cell cancer (i.e., large cell undifferentiated carcinoma).

Adenocarcinoma is a cancer that develops in the lining or inner surface of an organ. Adenocarcinoma is the most common type of lung cancer, making up 30%-40% of all cases of lung cancer. A subtype of adenocarcinoma is called bronchoalveolar cell carcinoma, which creates a pneumonia-like appearance on chest X-rays.

Squamous cell carcinoma is a cancer that begins in squamous cells. Squamos cells are thin, flat cells that look under the microscope like fish scales. Squamous cells are found in the tissue that forms the surface of the skin, the lining of hollow organs of the body, and the passages of the respiratory and digestive tracts. Squamous cell carcinomas may arise in any of these tissues. Squamous cell carcinoma is the second most common type of lung cancer, making up about 30% of all cases.

Large cell carcinoma shows no evidence of squamous or glandular maturation. Thus these tumors are often diagnosed by default, when all other possibilities have been excluded. These tumors lack any diagnostic features to suggest their diagnosis prior to biopsy. They tend to grow rapidly, metastasize early, and are strongly associated with smoking. Large cell tumors are usually large, bulky, well-circumscribed, pink-grey masses with extensive hemorrhage and necrosis. Although they commonly have central necrosis, they rarely cavitate. They tend to present in the mid to peripheral lung zones. They may extend locally to involve the segmental or subsegmental bronchi. A variant of large cell carcinoma is giant cell carcinoma. This subtype is particularly aggressive and carries a very poor prognosis. These tumors generally present as a large peripheral mass with a focal necrotic component. They do not involve the large airways, unless by direct extension. Large cell cancer makes up 10%-20% of all cases of lung cancer.

Melanoma

Melanoma is a malignant tumor of melanocytes, which are the cells that make the pigment melanin and are derived from the neural crest. Although most melanomas arise in the skin, they may also arise from mucosal surfaces or at other sites to which neural crest cells migrate, including the uveal tract. Uveal melanomas differ significantly from cutaneous melanoma in incidence, prognostic factors, molecular characteristics, and treatment.

In the United States in 2014, 9,710 people were projected to die from melanoma, and numbers of new cases were estimated to be 76,100. Skin cancer is the most common malignancy diagnosed in the United States, with 3.5 million cancers diagnosed in 2 million people annually. Melanoma represents less than 5% of skin cancers but results in most deaths. The incidence has been increasing over the past four decades. Elderly men are at highest risk; however, melanoma is the most common cancer in young adults aged 25 to 29 years and the second most common cancer in those aged 15 to 29 years. Ocular melanoma is the most common cancer of the eye, with approximately 2,000 cases diagnosed annually.

Melanoma occurs predominantly in adults, and more than 50% of the cases arise in apparently normal areas of the skin. Although melanoma can occur anywhere, including on mucosal surfaces and the uvea, melanoma in women occurs more commonly on the extremities, and in men it occurs most commonly on the trunk or head and neck.

Prognosis is affected by the characteristics of primary and metastatic tumors. The most important prognostic factors include, but are not limited to, the following: thickness or level of invasion of the melanoma, mitotic index, defined as mitoses per millimeter, ulceration or bleeding at the primary site, number of regional lymph nodes involved, with distinction of macrometastasis and micrometastasis, systemic metastasis, site—nonvisceral versus lung versus all other visceral sites, elevated serum lactate dehydrogenase level. Without being bound by any theory, it is contemplated that the presence of tumor infiltrating lymphocytes can be a potential prognostic factor.

Breast Cancer

Breast cancer is cancer that develops from breast tissue. Signs of breast cancer may include a lump in the breast, a change in breast shape, dimpling of the skin, fluid coming from the nipple, or a red scaly patch of skin. In those with distant spread of the disease, there may be bone pain, swollen lymph nodes, dyspnea, or jaundice. Outcomes for breast cancer vary depending on the cancer type, extent of disease, and subject age. Worldwide, breast cancer is the leading type of cancer in women, accounting for 25% of all cases. In 2012 it resulted in 1.68 million cases and 522,000 deaths. It is more common in developed countries and is more than 100 times more common in women than in men. Breast cancers are classified by several grading systems. Each of these systems can influence the prognosis and can affect treatment. Breast cancer is usually classified primarily by its histological appearance. Most breast cancers are derived from the epithelium lining the ducts or lobules, and these cancers are classified as ductal or lobular carcinoma. Carcinoma in situ is growth of low grade cancerous or precancerous cells within a particular tissue compartment such as the mammary duct without invasion of the surrounding tissue. In contrast, invasive carcinoma does not confine itself to the initial tissue compartment.

Breast cancer staging using the TNM system is based on the size of the tumor (T), whether or not the tumor has spread to the adjacent lymph nodes (N), and whether the tumor has metastasized (M) to a more distant part of the body. Larger size, nodal spread, and metastasis have a larger stage number and a worse prognosis. The main stages are stage 0, stages 1-3, and stage 4. Stage 0 is a pre-cancerous or marker condition, either ductal carcinoma in situ (DCIS) or lobular carcinoma in situ (LCIS). Stages 1-3 are within the breast or regional lymph nodes. Stage 4 is metastatic cancer that has a less favorable prognosis.

Breast cancer cells have receptors on their surface and in their cytoplasm and nucleus. Chemical messengers such as hormones bind to receptors, and this causes changes in the cell. Breast cancer cells can or cannot have three important receptors: estrogen receptor (ER), progesterone receptor (PR), and HER2. This leads to a division of breast cancers into hormone receptor-positive breast cancers or ER-/PR-positive breast cancers, HER2-positive breast cancers, and triple negative breast cancers, which are negative for ER, PR, and HER2.

Myeloid derived suppressor cells have been shown to have several important clinical correlations in breast cancer. In pre-clinical models of breast cancer, myeloid derived suppressor cell levels positively correlate with tumor size and inversely correlate with T cells. In the clinic, baseline levels of circulating myeloid derived suppressor cells correlate with disease burden, metastatic spread, and reduced survival in metastatic breast cancer. Baseline levels of circulating myeloid derived suppressor cells have been shown to correlate with response to adjuvant chemotherapy in HER2-negative breast cancer, with increasing levels indicating poorer response to chemotherapy.

Hormone Receptor-Positive Breast Cancer

Hormones, such as estrogen and progesterone, promote the growth of cancers that are hormone receptor-positive. About two out of three of breast cancers are hormone receptor-positive, as they contain receptors for the hormones estrogen (ER-positive breast cancers) or progesterone (PR-positive breast cancers). As these breast cancers depend upon the hormones for growth, therapies have been designed to either lower estrogen levels or stop estrogen activity breast cancer cells.

Non-limiting examples of therapies that stop estrogen activity include tamoxifen, toremifene, and fulvestrant. Tamoxifen blocks estrogen binding to estrogen receptors in breast cancer cells. While tamoxifen acts like an anti-estrogen in breast cells, it functions like an estrogen in other tissues, like the uterus and the bones. Because it acts like estrogen in some tissues but like an anti-estrogen in others, it is called a selective estrogen receptor modulator (SERM). Toremifene is another SERM that is approved to treat metastatic breast cancer. Fulvestrant is a drug that first blocks the estrogen receptor and triggers its degradation. Fulvestrant is not a SERM, as it acts like an anti-estrogen throughout the body. Fulvestrant is used to treat metastatic breast cancer after other hormone therapies, for example, tamoxifen, have stopped working.

Aromatase inhibitors (AIs) function to block estrogen production in post-menopausal women. Aromatase inhibitors work by blocking aromatase, which converts androgens generated by adipose tissue and the brain. Non-limiting examples of aromatase inhibitors include letrozole, anastrozole, and exemestane.

Triple Negative Breast Cancer

Triple-negative breast cancer, characterized by tumors that do not express estrogen receptor (ER), progesterone receptor (PR), or HER-2 genes, represents an important clinical challenge because these cancers do not respond to endocrine therapy or other available targeted agents. The metastatic potential in triple-negative breast cancer is similar to that of other breast cancer subtypes, but these tumors are associated with a shorter median time to relapse and death. One important goal is therefore the identification of prognostic factors and markers to reliably select high and low risk subsets of patients with triple-negative disease for different treatment approaches of subtypes with differential responsiveness to specific agents. However, a reliable prognostic marker has been elusive, and markers have been inconsistently useful. For example, epidermal growth factor receptor (EGFR) has been studied, but there is still a lack of agreement on a standard assay or cutoff for EGFR expression levels with respect to prognosis. Similarly, because triple-negative status is sometimes used as a surrogate for basal-like breast cancer, specific basal markers have been explored. Indeed, trials designed to accrue patients with basal-like breast cancer using ER/PR and HER-2 negativity may provide only an approximation of the triple-negative population and are sometimes reanalyzed using more specific indicators like CK 5/6, EGFR status, and others, again marred by discordances.

Chemotherapy remains the mainstay of treatment of triple-negative breast cancer, but important limitations still need to be overcome in the next few years if any significant clinical strides are to be made. Current treatment strategies for triple-negative disease include anthracyclines, taxanes, ixabepilone, platinum agents, and biologic agents. More recently, EGFR inhibition has been proposed as a therapeutic mechanism in triple-negative breast cancer, again with mixed results. Agents that target poly(ADP-ribose) polymerase and androgen receptors have also been proposed in these patients or subsets of them, and ongoing trials should result in definitive guidance with respect to the value of these agents in triple-negative disease. Triple-negative breast cancer is clearly a distinct clinical subtype, from the perspective of both ER and HER-2 expression, but further subclassification is needed. At present, there is not a clear, proven effective single agent that targets a defining vulnerability in triple-negative breast cancer.

Various subtypes of triple negative breast cancer includes basal like TNBC (Basal like 1 and 2 (BL-1, BL-2), Immunomodulatory (IM)) and mesenchymal stem like triple negative breast cancer (MSL), and luminal androgen receptor (LAR) subtype.

PD-L1 is expressed on many cancers including renal cell carcinoma, pancreatic cancer, ovarian cancer, gastric cancer, esophageal cancer, and hepatocellular carcinoma. Research has identified the expression of PD-L1 in 50% (22 out of 44 of tumors evaluated in a breast cancer study). In 15 (34%) it was restricted to the tumor epithelium, whereas in 18 (41%) it was identified in tumor infiltrating lymphocytes. Furthermore, it was found that intratumoral expression of PD-L1 was associated with high histologic grade and negative hormone receptor status. Consistent with the previous study, it was also in a separate study that approximately 20% of TNBC tumors express PD-L1. The majority (95%) of these TNBC tumors were grade 3.

Without being bound by any specific theory it is hypothesized that a possible mechanism by which tumors can drive PD-L1 expression is by oncogenic signaling pathways. This was first demonstrated in glioblastomas where it was observed that PTEN loss was associated with increased PD-L1 expression, suggesting the involvement of the PI3K pathway. Because PTEN loss is commonly seen in TNBC, a study investigated the relationship between PTEN and PD-L1 expression. In approximately 50% of TNBC tumors included in the breast cancer tissue microarrays where there was >5% PD-L1 expression, a loss of PTEN staining was observed. Similarly, in a panel of TNBC cell lines, it was found that two exemplary cell lines with PTEN loss, MDA-MB-468 and BT-549, had high cell surface PD-L1 expression. Together, these data suggested that there are likely multiple mechanisms of PD-L1 regulation in TNBC.

Ovarian Cancer

Ovarian cancer is the eighth most common cancer in women worldwide with estimated 225,500 new diagnoses per year and estimated 140,200 deaths per year.

There are three basic types of ovarian tumors: epithelial, germ cell, and stromal cell tumors. Epithelial tumors start from the cells that cover the outer surface of the ovary; most ovarian tumors are epithelial cell tumors. Germ cell tumors start from the cells that produce the eggs. Stromal tumors start from cells that hold the ovary together and make the female hormones. A significant risk factor for ovarian cancer includes deficiencies in DNA repair via homologous recombination, such as mutations in the BRCA1 or BRCA2 gene. Those genes were originally identified in families with multiple cases of breast cancer, but have been associated with approximately 5 to 10 percent of ovarian cancers.

Possible treatments for ovarian cancer include surgery, immunotherapy, chemotherapy, hormone therapy, radiation therapy, or a combination thereof. Surgical procedures for the treatment of ovarian cancer include debulking, and a unilateral or bilateral oophorectomy and/or a unilateral or bilateral salpigectomy. Anti-cancer drugs that have also been used to treat ovarian cancer include cyclophosphamide, etoposide, altretamine, and ifosfamide. Hormone therapy with the drug tamoxifen is also used to shrink ovarian tumors. Radiation therapy optionally includes external beam radiation therapy and/or brachytherapy. The majority of newly-diagnosed ovarian cancer patients have been shown to respond to first-line platinum-based and paclitaxel chemotherapy. However, 50-80% of the patients who respond to this combination therapy will eventually relapse. See, e.g., Herzog, "Update on the role of topotecan in the treatment of recurrent ovarian cancer," The Oncologist 7(Suppl. 5):3-10 (2002). Women with advanced ovarian cancer have poor long-term survival due to disease recurrence and most die within 5 years. Ovarian cancer relapsing within 6 months of platinum treatment represents a heterogeneous spectrum of disease with a low response rate to therapy (~10%-25%), generally of short duration. Attempts to identify patients who will respond to specific drugs are challenging. There is clearly a need to improve the current treatment options for recurrent ovarian cancer.

The terms "heavily pre-treated recurrent ovarian cancer" and "platinum-resistant ovarian carcinoma", as used herein, refer to ovarian cancer that has been treated with one or more rounds of platinum based chemotherapy using agents such as cisplatin, gemcitabine, carboplatin.

PD-L1 is expressed on many cancers including renal cell carcinoma, pancreatic cancer, ovarian cancer, gastric cancer, esophageal cancer, and hepatocellular carcinoma. It has been shown that PD-L1 expression on monocytes in the ascites and blood of patients with malignant ovarian cancer is strikingly higher than those with benign/borderline disease, with no overlap in the values between these groups. Furthermore, recent studies indicate that most ovarian cancers evade the host immune system and accelerate tumor growth by expressing PD-L1. Therefore, it is hypothesized that the PD-1/PD-L pathway may be a potential target for immunotherapy of ovarian cancer.

Methods of Selecting Patients for Combination Therapy

In certain embodiments, a method of the present disclosure comprises measuring CD14-positive, HLA-DR-high, and/or CD16-negative cells and measuring peripheral blood mononuclear cells to determine administration of a combination therapy to a patient diagnosed with a cancer.

In some embodiments, the method further comprises selecting the patient for combination therapy if the percentage of CD14-positive, HLA-DR-high and/or CD16– negative cells in the total peripheral blood mononuclear cells is greater than about 20%.

In some embodiments, the method further comprises selecting a patient that has progressed from previous treatment.

In some embodiments, the method further comprises selecting a combination therapy comprising entinostat and a second therapeutic agent.

Non-limiting examples of the second therapeutic agent include anti-PD-1 antibodies, for example, nivolumab and pembrolizumab; anti-PD-L1 antibodies, such as MPDL3280A; CTLA4-blocking antibodies, for example ipilimumab and tremelimumab. Non-limiting examples of the cancer include lung cancers, for example, non-small cell lung cancer, adenocarcinoma, squamous cell carcinoma, and large cell cancer (i.e., large cell undifferentiated carcinoma). In some embodiments, the second therapeutic agent is pembrolizumab and the cancer is a lung cancer. In some embodiments, the second therapeutic agent is pembrolizumab and the breast cancer is a non-small cell lung cancer. In some embodiments, the second therapeutic agent is pembrolizumab and the cancer is a melanoma.

In some embodiments, the entinostat is administered orally. In some embodiments, the entinostat is administered orally and the anti-PD-1 antibody, anti-PD-L1, or CTLA4-blocking antibody is administered by an infusion. Non-limiting examples of infusions include subcutaneous infusion, intravenous infusion, intraperitoneal infusion, and infusion by osmotic pump.

In some embodiments, the entinostat is administered first in the combination therapy. In some embodiments, the entinostat is administered weekly. In some embodiments, the entinostat is administered every two weeks.

Entinostat, anti-PD-1 antibody, anti-PD-L1, or CTLA4-blocking antibody can be administered about every day, about every two days, about every three days, about every four days, about every five days, about every six days, about every week, about every two weeks, about every three weeks, about every four weeks, about every month, about every five weeks, about every six weeks, about every seven weeks, about every eight weeks, or about every two months. Entinostat, anti-PD-1 antibody, anti-PD-L1, or CTLA4-blocking antibody can be administered from about every day to about every two days, from about every two days to about every three days, from about every three days to about every four days, from about every four days to about every five days, from about every five days to about every six days, from about every six days to about every week, from about every week to about every two weeks, from about every two weeks to about every three weeks, from about every three weeks to about every four weeks, from about every four weeks to about every month, from about every month to about every five weeks, from about every five weeks to about every six weeks, from about every six weeks to about every seven weeks, from about every seven weeks to about every eight weeks, or from about every eight weeks to about every two months.

In some embodiments, the CD14-positive, HLA-DR-high, and/or CD16-negative and peripheral blood mononuclear cells are circulating and are each measured in peripheral blood by obtaining a peripheral blood sample. In some embodiments, the peripheral blood sample is treated with an anticoagulant. In some embodiments, the peripheral blood sample is collected in or transferred into an anticoagulant-containing container. Non-limiting examples of anticoagulants include heparin, sodium heparin, potassium oxalate, EDTA, and sodium citrate. In some embodiments, the peripheral blood sample is treated with a red blood cell lysis agent. In some embodiments, the peripheral blood mononuclear cells are measured in tissue biopsies.

In some embodiments, a number of CD14-positive, HLA-DR-high, and/or CD16-negative cells, and peripheral blood mononuclear cells are measured in the peripheral blood sample and a percentage of CD14-positive, HLA-DR-high, and/or CD16-negative cells in total peripheral blood mononuclear cells is determined.

In some embodiments, the percentage of CD14-positive, HLA-DR-high and/or CD16-negative cells relative to total peripheral blood mononuclear cells is utilized to select patients for administering a combination therapy comprising an HDAC inhibitor and a second therapeutic agent.

CD14-Positive

In some embodiments, the percentage of CD14-positive cells relative to total peripheral blood mononuclear cells in a peripheral blood sample or a tissue biopsy is at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 45%, at least about 50%, at least about 60%, at least about 70%, at least about 80%, at least about 90%, at least about 95%, at least about 96%, at least about 97%, at least about 98%, or at least about 99%.

In some embodiments, the percentage of CD14-positive cells relative to total peripheral blood mononuclear cells in a peripheral blood sample or a tissue biopsy is from about 10% to about 20%, from about 10% to about 25%, from about 10% to about 30%, from about 10% to about 35%, from about 10% to about 40%, from about 10% to about 45%, from about 10% to about 50%, from about 15% to about 20%, from about 15% to about 25%, from about 15% to about 30%, from about 15% to about 35%, from about 15% to about 40%, from about 15% to about 45%, from about 15% to about 50%, from about 20% to about 25%, from about 20% to about 30%, from about 20% to about 35%, from about 20% to about 40%, from about 20% to about 45%, from about 20% to about 50%, from about 25% to about 30%, from about 25% to about 35%, from about 25% to about 40%, from about 25% to about 45%, from about 25% to about 50%, from about 30% to about 35%, from about 30% to about 40%, from about 30% to about 45%, from about 30% to about 50%, from about 35% to about 40%, from about 35% to about 45%, from about 35% to about 50%, from about 40% to about 45%, from about 40% to about 50%, from about 45% to about 50%.

HLA-DR-High

In some embodiments, the percentage of HLA-DR-high cells relative to total peripheral blood mononuclear cells in a peripheral blood sample or a tissue biopsy is at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 45%, at least about 50%, at least about 60%, at least about 70%, at least about 80%, at least about 90%, at least about 95%, at least about 96%, at least about 97%, at least about 98%, or at least about 99%.

In some embodiments, the percentage of HLA-DR-high cells relative to total peripheral blood mononuclear cells in a peripheral blood sample or a tissue biopsy is from about 10% to about 20%, from about 10% to about 25%, from about 10% to about 30%, from about 10% to about 35%, from about 10% to about 40%, from about 10% to about 45%, from about 10% to about 50%, from about 15% to about 20%, from about 15% to about 25%, from about 15% to about 30%, from about 15% to about 35%, from about 15% to about 40%, from about 15% to about 45%, from about 15% to about 50%, from about 20% to about 25%, from about 20% to about 30%, from about 20% to about 35%, from about 20% to about 40%, from about 20% to about 45%, from about 20% to about 50%, from about 25% to about 30%, from about 25% to about 35%, from about 25% to about 40%, from about 25% to about 45%, from about 25% to about 50%, from about 30% to about 35%, from about 30% to about 40%, from about 30% to about 45%, from about 30% to about 50%, from about 35% to about 40%, from about 35% to about 45%, from about 35% to about 50%, from about 40% to about 45%, from about 40% to about 50%, from about 45% to about 50%.

CD16-Negative

In some embodiments, the percentage of CD16-negative cells relative to total peripheral blood mononuclear cells in a peripheral blood sample or a tissue biopsy is at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 45%, at least about 50%, at least about 60%, at least about 70%, at least about 80%, at least about 90%, at least about 95%, at least about 96%, at least about 97%, at least about 98%, or at least about 99%.

In some embodiments, the percentage of CD16-negative cells relative to total peripheral blood mononuclear cells in a peripheral blood sample or a tissue biopsy is from about 10% to about 20%, from about 10% to about 25%, from about 10% to about 30%, from about 10% to about 35%, from about 10% to about 40%, from about 10% to about 45%, from about 10% to about 50%, from about 15% to about 20%, from about 15% to about 25%, from about 15% to about 30%, from about 15% to about 35%, from about 15% to about 40%, from about 15% to about 45%, from about 15% to about 50%, from about 20% to about 25%, from about 20% to about 30%, from about 20% to about 35%, from about 20% to about 40%, from about 20% to about 45%, from about 20% to about 50%, from about 25% to about 30%, from about 25% to about 35%, from about 25% to about 40%, from about 25% to about 45%, from about 25% to about 50%, from about 30% to about 35%, from about 30% to about 40%, from about 30% to about 45%, from about 30% to about 50%, from about 35% to about 40%, from about 35% to about 45%, from about 35% to about 50%, from about 40% to about 45%, from about 40% to about 50%, from about 45% to about 50%.

CD14-Positive and HLA-DR-High

In some embodiments, the percentage of CD14-positive and HLA-DR-high cells relative to total peripheral blood mononuclear cells in a peripheral blood sample or a tissue biopsy is at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 45%, at least about 50%, at least about 60%, at least about 70%, at least about 80%, at least about 90%, at least about 95%, at least about 96%, at least about 97%, at least about 98%, or at least about 99%.

In some embodiments, the percentage of CD14-positive and HLA-DR-high cells relative to total peripheral blood mononuclear cells in a peripheral blood sample or a tissue biopsy is from about 10% to about 20%, from about 10% to about 25%, from about 10% to about 30%, from about 10% to about 35%, from about 10% to about 40%, from about 10% to about 45%, from about 10% to about 50%, from about 15% to about 20%, from about 15% to about 25%, from about 15% to about 30%, from about 15% to about 35%, from about 15% to about 40%, from about 15% to about 45%, from about 15% to about 50%, from about 20% to about 25%, from about 20% to about 30%, from about 20% to about 35%, from about 20% to about 40%, from about 20% to about 45%, from about 20% to about 50%, from about 25% to about 30%, from about 25% to about 35%, from about 25% to about 40%, from about 25% to about 45%, from about 25% to about 50%, from about 30% to about 35%, from about 30% to about 40%, from about 30% to about 45%, from about 30% to about 50%, from about 35% to about 40%, from about 35% to about 45%, from about 35% to about 50%, from about 40% to about 45%, from about 40% to about 50%, from about 45% to about 50%.

CD14-Positive and CD16-Negative

In some embodiments, the percentage of CD14-positive and CD16-negative cells relative to total peripheral blood mononuclear cells in a peripheral blood sample or a tissue biopsy is at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 45%, at least about 50%, at least about 60%, at least about 70%, at least about 80%, at least about 90%, at least about 95%, at least about 96%, at least about 97%, at least about 98%, or at least about 99%.

In some embodiments, the percentage of CD14-positive and CD16-negative cells relative to total peripheral blood mononuclear cells in a peripheral blood sample or a tissue biopsy is from about 10% to about 20%, from about 10% to about 25%, from about 10% to about 30%, from about 10% to about 35%, from about 10% to about 40%, from about 10% to about 45%, from about 10% to about 50%, from about 15% to about 20%, from about 15% to about 25%, from about 15% to about 30%, from about 15% to about 35%, from about 15% to about 40%, from about 15% to about 45%, from about 15% to about 50%, from about 20% to about 25%, from about 20% to about 30%, from about 20% to about 35%, from about 20% to about 40%, from about 20% to about 45%, from about 20% to about 50%, from about 25% to about 30%, from about 25% to about 35%, from about 25% to about 40%, from about 25% to about 45%, from about 25% to about 50%, from about 30% to about 35%, from about 30% to about 40%, from about 30% to about 45%, from about 30% to about 50%, from about 35% to about 40%, from about 35% to about 45%, from about 35% to about 50%, from about 40% to about 45%, from about 40% to about 50%, from about 45% to about 50%.

HLA-DR-High and CD16-Negative

In some embodiments, the percentage of HLA-DR-high and CD16-negative cells relative to total peripheral blood mononuclear cells in a peripheral blood sample or a tissue biopsy is at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 45%, at least about 50%, at least about 60%, at least about 70%, at least about 80%, at least about 90%, at least about 95%, at least about 96%, at least about 97%, at least about 98%, or at least about 99%.

In some embodiments, the percentage of HLA-DR-high and CD16-negative cells relative to total peripheral blood mononuclear cells in a peripheral blood sample or a tissue biopsy is from about 10% to about 20%, from about 10% to about 25%, from about 10% to about 30%, from about 10% to about 35%, from about 10% to about 40%, from about 10% to about 45%, from about 10% to about 50%, from about 15% to about 20%, from about 15% to about 25%, from about 15% to about 30%, from about 15% to about 35%, from about 15% to about 40%, from about 15% to about 45%, from about 15% to about 50%, from about 20% to about 25%, from about 20% to about 30%, from about 20% to about 35%, from about 20% to about 40%, from about 20% to about 45%, from about 20% to about 50%, from about 25% to about 30%, from about 25% to about 35%, from about 25% to about 40%, from about 25% to about 45%, from about 25% to about 50%, from about 30% to about 35%, from about 30% to about 40%, from about 30% to about 45%, from about 30% to about 50%, from about 35% to about 40%, from about 35% to about 45%, from about 35% to about 50%, from about 40% to about 45%, from about 40% to about 50%, from about 45% to about 50%.

CD14-Positive, HLA-DR-High and CD16-Negative

In some embodiments, the percentage of CD14-positive, HLA-DR-high and CD16– negative cells relative to total peripheral blood mononuclear cells in a peripheral blood sample or a tissue biopsy is at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 45%, at least about 50%, at least about 60%, at least about 70%, at least about 80%, at least about 90%, at least about 95%, at least about 96%, at least about 97%, at least about 98%, or at least about 99%.

In some embodiments, the percentage of CD14-positive, HLA-DR-high, and CD16-negative cells relative to total peripheral blood mononuclear cells in a peripheral blood sample or a tissue biopsy is from about 10% to about 20%, from about 10% to about 25%, from about 10% to about 30%, from about 10% to about 35%, from about 10% to about 40%, from about 10% to about 45%, from about 10% to about 50%, from about 15% to about 20%, from about 15% to about 25%, from about 15% to about 30%, from about 15% to about 35%, from about 15% to about 40%, from about 15% to about 45%, from about 15% to about 50%, from about 20% to about 25%, from about 20% to about 30%, from about 20% to about 35%, from about 20% to about 40%, from about 20% to about 45%, from about 20% to about 50%, from about 25% to about 30%, from about 25% to about 35%, from about 25% to about 40%, from about 25% to about 45%, from about 25% to about 50%, from about 30% to about 35%, from about 30% to about 40%, from about 30% to about 45%, from about 30% to about 50%, from about 35% to about 40%, from about 35% to about 45%, from about 35% to about 50%, from about 40% to about 45%, from about 40% to about 50%, from about 45% to about 50%.

In some embodiments, a number of CD14-positive, HLA-DR-high, and/or CD16– negative cells per unit volume of a biological sample is determined. Non-limiting examples of unit volumes include picoliters (pL), nanoliters (nL), microliters (µL), milliliters (mL), deciliters (dL), and liters (L). In some embodiments, the number of CD14-positive, HLA-DR-high, and/or CD16-negative cells cells per unit volume of the biological sample is utilized to select patients for administering a combination therapy comprising HDAC inhibitor and a second therapeutic agent. In some embodiments, the biological sample is peripheral blood sample.

In some embodiments, the number of CD14-positive, HLA-DR-high, and/or CD16-negative cells per unit volume of the biological sample is about 1, about 2, about 3, about 4, about 5, about 6, about 7, about 8, about 9, about 10, about 15, about 20, about 25, about 30, about 35, about 40, about 45, about 50, about 60, about 70, about 80, about 90, about 100, about 150, about 200, about 250, about 300, about 350, about 400, about 450, about 500, about 600, about 700, about 800, about 900, about 1000, about 1500, about 2000, about 2500, about 3000, about 3500, about 4000, about 4500, about 5000, about 6000, about 7000, about 8000, about 9000, about 10000, about 15000, about 20000, about 25000, about 30000, about 35000, about 40000, about 45000, about 50000, about 60000, about 70000, about 80000, about 90000, or about 100000 per unit volume.

In some embodiments, the number of CD14-positive, HLA-DR-high, and/or CD16-negative cells per unit volume of the biological sample is from about 1 to about 2, from about 2 to about 3, from about 3 to about 4, from about 4 to about 5, from about 5 to about 6, from about 6 to about 7, from about 7 to about 8, from about 8 to about 9, from about 9 to about 10, from about 10 to about 15, from about 15 to about 20, from about 20 to about 25, from about 25 to about 30, from about 30 to about 35, from about 35 to about 40, from about 40 to about 45, from about 45 to about 50, from about 50 to about 60, from about 60 to about 70, from about 70 to about 80, from about 80 to about 90, from about 90 to about 100, from about 100 to about 150, from about 150 to about 200, from about 200 to about 250, from about 250 to about 300, from about 300 to about 350, from about 350 to about 400, from about 400 to about 450, from about 450 to about 500, from about 500 to about 600, from about 600 to about 700, from about 700 to about 800, from about 800 to about 900, from about 900 to about 1000, from about 1000 to about 1500, from about 1500 to about 2000, from about 2000 to about 2500, from about 2500 to about 3000, from about 3000 to about 3500, from about 3500 to about 4000, from about 4000 to about 4500, from about 4500 to about 5000, from about 5000 to about 6000, from about 6000 to about 7000, from about 7000 to about 8000, from about 8000 to about 9000, from about 9000 to about 10000, from about 10000 to about 15000, from about 15000 to about 20000, from about 20000 to about 25000, from about 25000 to about 30000, from about 30000 to about 35000, from about 35000 to about 40000, from about 40000 to about 45000, from about 45000 to about 50000, from about 50000 to about 60000, from about 60000 to about 70000, from about 70000 to about 80000, from about 80000 to about 90000, or from about 90000 to about 100000 per unit volume.

In some embodiments, CD14-positive, HLA-DR-high, and/or CD16-negative cells and peripheral blood mononuclear cells are measured using flow cytometry, mass cytometry, cytospin, or immunohistochemistry.

Flow cytometry is a laser-based technology used in cell counting, cell sorting, and biomarker detection, by suspending cells in a stream of fluid and passing them by an electronic detection apparatus. It allows simultaneous multiparametric analysis of the physical and chemical characteristics of up to thousands of particles per second.

Mass cytometry is a mass spectrometry technique based on inductively coupled plasma mass spectrometry for the determination cell identity and function. In this technology, binding agents are tagged with isotopically pure rare earth elements. These binding agents are then applied to tag cells and their components. Cells are nebulized and sent through an argon plasma laser, ionizing the multi-atom rare earth elemental tags. The ionized, tagged cells are then analyzed by a time-of-flight mass spectrometer. The advantage of mass cytometry is the capacity to overcome the limitations developed by spectral overlap in flow cytometry.

Cytospin is a technique in which suspension cells are centrifuged onto glass slides as a smear for cell staining and cell counting. Concentrated cell suspensions that exist in a low-viscosity medium make good candidates for smear preparations. Dilute cell suspensions existing in a dilute medium are best suited for the preparation of cytospins through cytocentrifugation. Cell suspensions that exist in a high-viscosity medium, are best suited to be tested as swab preparations. The constant among these preparations is that the whole cell is present on the slide surface.

Immunohistochemistry is a type of histological staining for detecting antigens in cells of a tissue section by exploiting the principle of antibodies binding specifically to antigens in biological tissues. Visualizing an antibody-antigen interaction can be accomplished in a number of ways. The antibody can be conjugated to an enzyme, such as peroxidase, that can catalyze a color-producing reaction. Alternatively, the antibody can be tagged to a fluorophore, such as fluorescein or rhodamine.

In some embodiments, CD14-positive, HLA-DR-high, and/or CD16-negative cells and peripheral blood mononuclear cells are identified by a cell surface marker. Non-limiting examples of cell surface markers that identify peripheral blood mononuclear cells include CD3, CD14, CD19, CD56, and HLA-DR.

In some embodiments, CD14-positive, HLA-DR-high, and/or CD16-negative cells are identified by CD14, a high level of HLA-DR and an absence of CD16 and peripheral blood mononuclear cells are identified by CD3. In some embodiments, CD14-positive, HLA-DR-high, and/or CD16-negative cells are identified by CD14 and a high level of HLA-DR and an absence of CD16 and peripheral blood mononuclear cells are identified by CD14. In some embodiments, CD14-positive, HLA-DR-high, and/or CD16-negative cells are identified by CD14 and a high level of HLA-DR and an absence of CD16 and peripheral blood mononuclear cells are identified by CD19. In some embodiments, CD14-positive, HLA-DR-high, and/or CD16-negative cells are identified by CD14 and a high level of HLA-DR and an absence of CD16 and peripheral blood mononuclear cells are identified by CD56. In some embodiments, CD14-positive, HLA-DR-high, and/or CD16-negative cells are identified by CD14 and a high level of HLA-DR and an absence of CD16 and peripheral blood mononuclear cells are identified by HLA-DR. In some embodiments, CD14-positive, HLA-DR-high, and/or CD16-negative cells are identified by CD14 and a high level of HLA-DR and an absence of CD16 and peripheral blood mononuclear cells are identified by CD3, CD14, CD19, CD56, and HLA-DR. In some embodiments, CD14-positive, HLA-DR-high, and/or CD16-negative cells are identified by CD14 and a high level of HLA-DR and an absence of CD16 and peripheral blood mononuclear cells are identified by CD14.

Additional Therapy

Available additional treatments for cancers described herein that may be advantageously employed in combination with the therapies disclosed herein include, without limitation, radiation therapy, chemotherapy, antibody therapy, and tyrosine kinase inhibitors as adjuvant therapy.

Radiation therapy is a cancer treatment that uses high-energy x-rays or other types of radiation to kill cancer cells or keep them from growing. Chemotherapy is a cancer treatment that uses drugs to stop the growth of cancer cells, either by killing the cells or by stopping them from dividing. When chemotherapy is taken by mouth or injected into a vein or muscle, the drugs enter the bloodstream and can reach cancer cells throughout the body (systemic chemotherapy). When chemotherapy is placed directly into the spinal column, an organ, or a body cavity such as the abdomen, the drugs mainly affect cancer cells in those areas (regional chemotherapy). The way the chemotherapy is given depends on the type and stage of the cancer being treated.

Different chemotherapeutic agents are known in the art for treating lung cancer. Cytoxic agents used for treating lung cancer include carboplatin (for example, Paraplatin®, Paraplat®), cisplatin (for example, Platinol®, Platinol-Aq®), crizotinib (for example Xalkori®), etoposide (for example Toposar®, VePesid®), etoposide Phosphate (for example Etopophos®), gemcitabine hydrochloride (for example Gemzar®), gemcitabine-cisplatin, methotrexate (for example Abitrexate®, Folex®, Folex Pfs®, Methotrexate Lpf®, Mexate®, Mexate-Aq®), paclitaxel (for example Taxol®), pemetrexed Disodium (for example Alimta®), topotecan hydrochloride (for example Hycamtin®), and erlotinib (for example Tarceva®).

Different agents are known in the art for treating melanoma, including aldesleukin (for example Proleukin®), dabrafenib (for example Tafinlar®), dacarbazine (for example DTIC-Dome®), recombinant Interferon Alfa-2b (for example Intron® A), Ipilimumab (for example Yervoy®), pembrolizumab (for example Keytruda®), Trametinib (for example Mekinist®), Nivolumab (for example Opdivo®), Peginterferon Alfa-2b (for example Pegintron®, Sylatron®), vemurafenib (for example Zelboraf®).

Different agents are known in the art for treating breast cancer, including aromatase inhibiors such as anastrazole (such as Arimidex®), exemestane (for example Aromasin®), fadrozole (such as Afema®), formestane (such as Lentaron®), letrozole (such as Ferrara®), vorozole (such as Rivizor®).

Monoclonal antibody therapy is a cancer treatment that uses antibodies made in the laboratory, from a single type of immune system cell. These antibodies can identify substances on cancer cells or normal substances that may help cancer cells grow. The antibodies attach to the substances and kill the cancer cells, block their growth, or keep them from spreading. Monoclonal antibodies are given by infusion. They may be used alone or to carry drugs, toxins, or radioactive material directly to cancer cells. Monoclonal antibodies are also used in combination with chemotherapy as adjuvant therapy.

Additional, illustrative, treatments that may be advantageously combined with the compositions and therapies disclosed herein may include, without limitation, administration of agents including, but not limited to lapatinib, alone or in combination with capecitabine, docetaxel, epirubicin, epothilone A, B or D, goserelin acetate, paclitaxel, pamidronate, bevacizumab, or trastuzumab.

In some embodiments, the additional therapy comprises chemotherapy comprising administering to the subject one or more of doxorubicin, cyclophosphamide, paclitaxel, lapatinib, capecitabine, trastuzumab, bevacizumab, gemcitabine, eribulin, or nab-paclitaxel.

Oral Formulations

Oral formulations containing the active pharmaceutical ingredients described herein may comprise any conventionally used oral forms, including: tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, syrups, buccal forms, and oral liquids. Capsules may contain mixtures of the active compound(s) with inert fillers or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. In some embodiments are surface modifying agents which include nonionic and anionic surface modifying agents. For example, surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

Oral Administration

As described herein, the combination therapy described herein can be given simultaneously or can be given in a staggered regimen, with the HDAC inhibitor or entinostat being given at a different time during the course of chemotherapy compared to the second pharmaceutical agent. This time differential may range from several minutes, hours, days, weeks, or longer between administrations of the two components. Therefore, the term combination does not necessarily mean administered at the same time or as a unitary dose, but that each of the components are administered during a desired treatment period. The agents may also be administered by different routes. As is typical for chemotherapeutic regimens, a course of chemotherapy may be repeated several weeks later, and may follow the same timeframe for administration of the two compounds, or may be modified based on patient response.

In other embodiments, the pharmaceutical compositions provided herein may be provided in solid, semisolid, or liquid dosage forms for oral administration. As used herein, oral administration also include buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

In further embodiments, the pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

In other embodiments, the pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfate, sodium metabisulfite, thiodipropionic acid and its esters, and dithiocarbamates.

The pharmaceutical compositions provided herein for oral administration may be also provided in the forms of liposomes, micelles, microspheres, or nanosystems. Micellar dosage forms can be prepared as described in U.S. Pat. No. 6,350,458.

In other embodiments, the pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein may be formulated as immediate or modified release dosage forms, including delayed-, sustained, pulsed-, controlled, targeted-, and programmed-release forms.

In further embodiments, the pharmaceutical compositions provided herein may be co-formulated with other active ingredients which do not impair the desired therapeutic action, or with substances that supplement the desired action. In some embodiments, the anti-PD-1 antibody, the anti-PD-L1 and/or the CTLA4-blocking therapeutic and the HDAC inhibitor are administered in temporal proximity (e.g., the anti-PD-1 antibody, the anti-PD-L1 and/or the CTLA4-blocking therapeutic and the HDAC inhibitor can be administered simultaneously). Accordingly, the present disclosure provides a method of treating or preventing cancer comprising administering the anti-PD-1 antibody, the anti-PD-L1 and/or the CTLA4-blocking therapeutic and the HDAC inhibitor in temporal proximity.

In some embodiments, "temporal proximity" means that administration of one therapeutic agent occurs within a time period before or after the administration of another therapeutic agent, such that the therapeutic effect of the one therapeutic agent overlaps with the therapeutic effect of the another therapeutic agent. In some embodiments, the therapeutic effect of the one therapeutic agent completely overlaps with the therapeutic effect of the other therapeutic agent. In some embodiments, "temporal proximity" means that administration of one therapeutic agent occurs within a time period before or after the administration of another therapeutic agent, such that there is a synergistic effect between the one therapeutic agent and the another therapeutic agent. "Temporal proximity" may vary according to various factors, including but not limited to, the age, gender, weight, genetic background, medical condition, disease history, and treatment history of the subject to which the therapeutic agents are to be administered; the disease or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, multiple administration of one therapeutic agent can occur in temporal proximity to a single administration of another therapeutic agent. In some embodiments, temporal proximity may change during a treatment cycle or within a dosing regimen.

EXAMPLES

Example 1. NSCLC Patient Selection for Entinostat Combination Therapy with Pembrolizumab To select a patient for combination treatment with HDAC inhibitor in combination with a second therapeutic agent, a peripheral blood sample is taken from the patient. The patient is diagnosed with non-small cell lung cancer who progressed during, or did not respond to, anti-PD-1 or anti-PD-L1 treatment. The 5 milliliter (mL) peripheral blood sample is taken into EDTA collection tubes, which are rapidly cooled on ice. Blood samples are transferred to a conical tube and diluted with 15 mL of red blood cell lysis buffer and incubated at room temperature for 10 minutes. Red blood cell lysis is quenched by dilution with 30 mL phosphate-buffered saline (PBS). The cell suspension is centrifuged 5 minutes at 400×g at 4° C. and the supernatant is discarded. The pellet is resuspended in 5 mL of PBS and transferred to a new conical tube. The resuspended sample is underlayed with 5 mL Ficoll®. Cells are centrifuged for 20 minutes 400×g with the brake turned off on the centrifuge. Nucleated cells are harvested at the interface of the PBS and Ficoll® layers into a fresh conical tube.

An equal volume to the original blood draw is added to the pellet in the fresh conical tube to wash the cells. The cell suspension is centrifuged 5 minutes at 400×g at 4° C. and the supernatant is discarded. Cells are resuspended in an equal volume to the original blood draw in PBS with 1% bovine serum albumin and 0.5% EDTA (staining buffer). Viable cells are then counted using a hemacytometer. The cell suspension is centrifuged 5 minutes at 400×g at 4° C., the supernatant is discarded, and the cells are resuspended in Staining Buffer to a cell concentration of about $10^7$ cells per mL and 1 mL aliquots are transferred to new tubes.

The following antibodies are added to the resuspended cells: FITC-conjugated anti-CD14; PE-conjugated anti-HLA-DR; and APC-conjugated anti-CD3, anti-CD19, and anti-CD56. Control samples include unstained cells and stained cells in which one of each of the set of fluorochrome antibodies is left out. Cells are covered to minimize light exposure and left at room temperature for 20 minutes. Stained cells are washed twice in staining buffer by centrifugation for 5 minutes at 400×g at 4° C., discarding of the supernatant, and resuspension in an equal volume of staining buffer. Stained cells are then transferred to polypropylene tubes for use on the flow cytometer.

Flow cytometry is performed on a Cytomics FC 500 flow cytometer, which automates tube-based acquisition of flow cytometry data. After performance of the automated run, samples are corrected both for background fluorescence (using the unstained sample) and fluorochrome compensation (using the individually left out fluorochrome samples). CD14-positive, HLA-DR-high and CD16-negative cells are identified by CD14 positivity, HLA-DR high expression, and CD16, CD3, CD19, and CD56 negativity. Peripheral blood mononuclear cells, identified by CD3, CD19 and CD56 positivity. These values are used to calculate the percentage of CD14-positive, HLA-DR-high, and/or CD16-negative cells in total peripheral blood mononuclear cells. In this setting, if the patient has a percentage of CD14-positive, HLA-DR-high, and CD16-negative cells between at least 5% and 100%, indicating the presence of elevated numbers of CD14-positive, HLA-DR-high and CD16-negative cells the patient is selected for combination therapy with entinostat and pembrolizumab.

Example 2. Melanoma Patient Selection for Entinostat Combination Therapy with Pembrolizumab To select a patient for combination treatment with entinostat combination therapy with pembrolizumab, a peripheral blood sample is taken from the patient. The patient is diagnosed with a melanoma who progressed during, or did not respond to, anti-PD-1 or anti-PD-L1 treatment. The 5 milliliter (mL) peripheral blood sample is taken into EDTA collection tubes, which are rapidly cooled on ice. Blood samples are transferred to a conical tube and diluted with 15 mL of red blood cell lysis buffer and incubated at room temperature for 10 minutes. Red blood cell lysis is quenched by dilution with 30 mL phosphate-buffered saline (PBS). The cell suspension is centrifuged 5 minutes at 400×g at 4° C. and the supernatant is discarded. The pellet is resuspended in 5 mL of PBS and transferred to a new conical tube. The resuspended sample is underlayed with 5 mL Ficoll®. Cells are centrifuged for 20 minutes 400×g with the brake turned off on the centrifuge. Nucleated cells are harvested at the interface of the PBS and Ficoll® layers into a fresh conical tube.

An equal volume to the original blood draw is added to the pellet in the fresh conical tube to wash the cells. The cell suspension is centrifuged 5 minutes at 400×g at 4° C. and the supernatant is discarded. Cells are resuspended in an equal volume to the original blood draw in PBS with 1% bovine serum albumin and 0.5% EDTA (staining buffer). Viable cells are then counted using a hemacytometer. The cell suspension is centrifuged 5 minutes at 400×g at 4° C., the supernatant is discarded, and the cells are resuspended in Staining Buffer to a cell concentration of about $10^7$ cells per mL and 1 mL aliquots are transferred to new tubes.

The following antibodies are added to the resuspended cells: FITC-conjugated anti-CD14; PE-conjugated anti-HLA-DR; and APC-conjugated anti-CD3, anti-CD19, and anti-CD56. Control samples include unstained cells and stained cells in which one of each of the set of fluorochrome antibodies is left out. Cells are covered to minimize light exposure and left at room temperature for 20 minutes. Stained cells are washed twice in staining buffer by centrifugation for 5 minutes at 400×g at 4° C., discarding of the supernatant, and resuspension in an equal volume of staining buffer. Stained cells are then transferred to polypropylene tubes for use on the flow cytometer.

Flow cytometry is performed on a Cytomics FC 500 flow cytometer, which automates tube-based acquisition of flow cytometry data. After performance of the automated run, samples are corrected both for background fluorescence (using the unstained sample) and fluorochrome compensation (using the individually left out fluorochrome samples). CD14-positive, HLA-DR-high and CD16-negative cells are identified by CD14 positivity, HLA-DR high expression, and CD16, CD3, CD19, and CD56 negativity. Peripheral blood mononuclear cells, identified by CD3, CD19 and CD56 positivity. These values are used to calculate the percentage of CD14-positive, HLA-DR-high, and CD16-negative cells in total peripheral blood mononuclear cells. In this setting, if the patient has a percentage of CD14-positive, HLA-DR-high, and CD16-negative cells between at least 5% and 100%, indicating the presence of elevated numbers of CD14-positive, HLA-DR-high, and CD16-negative cells the patient is selected for combination therapy with entinostat and pembrolizumab.

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of selecting a patient for combination therapy comprising entinostat and an anti-PD-1 antibody comprising:

providing a peripheral blood sample obtained from the patient, wherein the patient is diagnosed with a cancer;

measuring the number of cells in the peripheral blood sample which are CD14-positive, HLA-DR-high, and CD16-negative;

measuring the number of total peripheral blood mononuclear cells in the peripheral blood sample; and administering the combination therapy if the percentage of the CD14-positive, HLA-DR-high, and CD16-negative cells relative to total peripheral blood mononuclear cells is greater than a pre-determined percentage; wherein the pre-determined percentage is at least about 5%.

2. The method of claim 1, wherein the patient progressed on a prior therapy with an anti-PD-1 antibody, an anti-PD-L1 antibody, a CTLA4-blocking antibody, or any combinations thereof.

3. The method of claim 2, wherein the patient previously was considered unresponsive to the at least one prior therapy.

4. The method of claim 1, wherein the peripheral blood sample is treated with an anticoagulant.

5. The method of claim 4, wherein the anticoagulant is EDTA or heparin.

6. The method of claim 1, wherein the pre-determined percentage is at least about 10%, at least about 15%, at least about 20%, at least about 25%, at least about 30%, at least about 35%, at least about 40%, at least about 45% or at least about 50%.

7. The method of claim 1, wherein entinostat is administered first.

8. The method of claim 7, wherein the entinostat is administered orally.

9. The method of claim 7, wherein the entinostat is administered weekly or every two weeks.

10. The method of claim 7, wherein the entinostat is administered once every week during the treatment cycle, at a dose of 3 mg or at a dose of 5 mg.

11. The method of claim 1, wherein the anti-PD-1 antibody is pembrolizumab.

12. The method of claim 1, wherein the cancer is a lung cancer, a melanoma, a breast cancer, or an ovarian cancer.

13. The method of claim 12, wherein:
   (a) the lung cancer is a non-small cell lung cancer, squamous cell carcinoma, or large cell carcinoma;
   (b) the melanoma is a metastatic melanoma; and
   (c) the breast cancer is a triple-negative breast cancer or hormone receptor positive breast cancer.

14. The method of claim 1, wherein entinostat and the anti-PD-1 antibody are administered sequentially in either order or simultaneously.

15. The method of claim 1, wherein the anti-PD-1 antibody is administered by infusion.

16. The method of claim 1, wherein the patient has received at least one round of a prior therapy.

17. The method of claim 1, wherein the patient has received at least three rounds of a prior therapy.

18. A method of selecting a patient for combination therapy comprising an entinostat and pembrolizumab comprising:

providing a peripheral blood sample from the patient, wherein the patient is diagnosed with non-small cell lung cancer and/or melanoma and progressed on and/or was considered unresponsive to prior PD-1 or PD-L1 therapy;

measuring the number of cells in the peripheral blood sample which are CD14-positive, HLA-DR-high, and CD16-negative;

measuring the number of total peripheral blood mononuclear cells in the peripheral blood sample; and administering the combination therapy if the percentage of CD14-positive, HLA-DR-high, and CD16-negative cells relative to total live peripheral blood mononuclear cells is greater than a pre-determined percentage; wherein the pre-determined percentage is at least about 5%.

* * * * *